(12) United States Patent
Furuta et al.

(10) Patent No.: US 8,419,915 B2
(45) Date of Patent: Apr. 16, 2013

(54) GAS SENSOR

(75) Inventors: Nobuo Furuta, Aichi (JP); Shigeki Mori, Seki (JP)

(73) Assignee: NGK Spark Plug Co., Ltd., Aichi (JP)

( * ) Notice: Subject to any disclaimer, the term of this patent is extended or adjusted under 35 U.S.C. 154(b) by 165 days.

(21) Appl. No.: 12/265,833

(22) Filed: Nov. 6, 2008

(65) Prior Publication Data

US 2009/0117007 A1 May 7, 2009

(30) Foreign Application Priority Data

Nov. 6, 2007 (JP) .............................. P2007-288932

(51) Int. Cl.
*G01N 27/406* (2006.01)
(52) U.S. Cl.
USPC ........... 204/424; 204/428; 204/429; 204/425; 204/426; 73/23.31; 73/23.32; 205/780.5; 205/781; 205/782
(58) Field of Classification Search .......... 204/424–429; 205/783.5–785, 781; 73/23.31–23.32
See application file for complete search history.

(56) References Cited

U.S. PATENT DOCUMENTS

| | | | |
|---|---|---|---|
| 5,194,135 A | 3/1993 | Hayakawa et al. | |
| 5,242,573 A | 9/1993 | Hayakawa et al. | |
| 6,156,176 A * | 12/2000 | Sugiyama et al. | 204/425 |
| 6,746,586 B2 | 6/2004 | Kuroki et al. | |
| 2002/0036138 A1* | 3/2002 | Kuroki et al. | 204/426 |
| 2002/0063059 A1* | 5/2002 | Sugiyama et al. | 204/426 |
| 2002/0070111 A1* | 6/2002 | Sugiyama et al. | 204/429 |
| 2003/0188969 A1* | 10/2003 | Imamura et al. | 204/424 |
| 2004/0084309 A1* | 5/2004 | Ando et al. | 204/426 |
| 2004/0154920 A1* | 8/2004 | Schneider et al. | 204/431 |
| 2006/0219554 A1* | 10/2006 | Mori et al. | 204/424 |
| 2007/0017806 A1* | 1/2007 | Furuta et al. | 204/424 |
| 2007/0084724 A1 | 4/2007 | Mori et al. | |

FOREIGN PATENT DOCUMENTS

JP       61-221644 A       10/1986
(Continued)

OTHER PUBLICATIONS

Communication dated Dec. 27, 2011 from the Japanese Patent Office in counterpart Japanese application No. 2007-288932.

(Continued)

*Primary Examiner* — Keith Hendricks
*Assistant Examiner* — Bach Dinh
(74) *Attorney, Agent, or Firm* — Sughrue Mion, PLLC

(57) ABSTRACT

A gas sensor including a detection element having a stacked structure configured to detect a specified gas component contained in a gas to be detected. The detection element includes: a sensing portion including one or more solid electrolyte layers containing a first material as a main component and having a first surface and a second surface opposite the first surface; a first portion stacked on the first surface and including one or more first base layers containing a second material as a main component different from the first material; and a second portion stacked on the second surface and including one or more second base layers containing the second material. A total thickness of the one or more second base layers in a stacking direction is not less than 80% but not more than 120% of a total thickness of the one or more first base layers.

14 Claims, 9 Drawing Sheets

FOREIGN PATENT DOCUMENTS

| | | |
|---|---|---|
| JP | 63-149551 A | 6/1988 |
| JP | 2000-206080 A | 7/2000 |
| JP | 2003107034 A | 4/2003 |
| JP | 2003-294687 A | 10/2003 |
| JP | 2003-294690 A | 10/2003 |
| JP | 2003-294697 A | 10/2003 |
| JP | 2003-294698 A | 10/2003 |
| JP | 2007-033374 A | 2/2007 |
| JP | 2007-139749 A | 6/2007 |

OTHER PUBLICATIONS

Communication from the Japanese Patent Office issued Aug. 28, 2012 in counterpart Japanese Application No. 2007-288932.

Japanese Office Action dated Jun. 19, 2012 issued by the Japanese Patent Office in counterpart Japanese Application No. 2007-288932.

* cited by examiner

GAS SENSOR

BACKGROUND OF THE INVENTION

1. Field of the Invention

The present invention relates to a gas sensor including a detection element configured to detect a specified gas component contained in a gas to be detected. An example of the gas sensor is one having a stacked detection element made by simultaneously sintering a plurality of stacked layers which contain different main components.

2. Description of the Related Art

The use of a gas sensor attached to an exhaust pipe of an automobile and including a detection element configured to vary an electromotive force or a resistance value according to the concentration of a specified component (for example, nitrogen oxide, oxygen, etc.) of exhaust gas is known. A stacked detection element manufactured by simultaneously sintering a plurality of stacked layers having different main components is also known. If the detection element is formed by simultaneous sintering, the sintering process is completed at one time, and a laminating process of layers is not required. Therefore, the number of processes can be remarkably reduced. For example, JP-A-2007-33374 or JP-A-2007-139749 describes a gas sensor having such a detection element.

JP-A-2007-33374 (FIG. 2 and related description in this reference) describes a gas sensor including a gas sensor element that includes a solid electrolyte layer configured to detect a specified gas component. A protection layer containing a main component different from the solid electrolyte layer is stacked on one surface of the solid electrolyte layer. Two insulating layers containing a main component different from the solid electrolyte layer are stacked on the other surface of the solid electrolyte layer. A total thickness of the two insulating layers is different from the protection layer.

The gas sensor element is manufactured as described below. That is, an unsintered solid electrolyte layer containing zirconia as a main component and becoming the solid electrolyte layer after sintering is formed. Two unsintered insulating layers containing alumina as a main component and becoming the insulating layers after sintering are formed. The unsintered insulating layers are stacked. An unsintered protection layer containing alumina as a main component and becoming a protection layer after sintering is formed. The unsintered solid electrolyte layer, the two unsintered insulating layers and the unsintered protection layer are stacked to form an unsintered stacked body. Thereafter, the unsintered stacked body is integrally sintered (simultaneously sintered) to obtain a gas sensor element.

JP-A-2007-139749 (FIG. 2 and related description in this reference) describes a gas sensor element including: a sensing portion including a first solid electrolyte layer and a second solid electrolyte layer, which are configured to detect a specified gas component; and an insulating layer stacked therebetween. A protection layer containing a main component different from a main component of the first and the second solid electrolyte layers is stacked on the second solid electrolyte layer. Two insulating layers containing a main component different from the main component of the first and the second solid electrolyte layers are stacked on the first solid electrolyte layer. A total thickness of the two insulating layers is different from the protection layer.

The gas sensor element is manufactured as described below. An unsintered first solid electrolyte layer containing zirconia as a main component and becoming the first solid electrolyte layer after sintering, and an unsintered second solid electrolyte layer containing zirconia as a main component and becoming the second solid electrolyte layer after sintering, are formed. An unsintered insulating layer containing alumina as a main component and becoming the insulating layer between the first solid electrolyte layer and the second electrolyte layer after sintering is formed. An unsintered protection layer containing alumina as a main component and becoming a protection layer after sintering is formed. Two unsintered insulating layers containing alumina as a main component and becoming an insulating layer after sintering are formed. The two unsintered insulating layers, the unsintered first solid electrolyte layer, the unsintered insulating layer, the unsintered second solid electrolyte layer and the unsintered protection layer are stacked in this order to form an unsintered stacked body. Thereafter, the unsintered stacked body is integrally sintered (simultaneously sintered) to obtain a gas sensor element.

However, the gas sensor element according to JP-A-2007-33374 and JP-A-2007-139749 may warp when sintered. This is because the shrinkage associated with sintering (hereinafter called a "sintering shrinkage") of solid electrolyte layers containing zirconia as a main component is largely different from that of other layers containing alumina as a main component. If the gas sensor element becomes warped, the gas sensor element may be subject to cracking or breakage. This is because the gas sensor element contacts other members when the gas sensor is manufactured by mounting other members to the gas sensor element.

Accordingly, it can be considered that a difference in sintering shrinkage between the solid electrolyte layers and other layers is reduced by changing the materials of the respective layers that constitute the gas sensor element in order to prevent a sintered gas sensor element from warping. However, taking the performance, strength and durability of the gas sensor element into consideration, there is a restriction in changing the materials. Heretofore, it has been difficult to sufficiently reduce the difference in sintering shrinkage so as to prevent warping while still maintaining good sensor performance and physical characteristics.

SUMMARY OF THE INVENTION

The present invention was made in consideration of the above problems of the prior art, and an object thereof is to provide a gas sensor having high reliability, in which the detection element is subject to less warping.

According to a first aspect, the present invention provides a stacking type gas sensor including a plate-shaped detection element formed by simultaneously sintering a plurality of layers stacked on one another and configured to detect a specified gas component in a gas to be detected. The detection element includes: a sensing portion configured to detect the specified gas component and having a first surface and a second surface opposite the first surface, the sensing portion comprising one or more solid electrolyte layers containing a first material as a main component; a first portion stacked on the first surface of the sensing portion and comprising one or more first base layers containing a second material as a main component different from the first material; and a second portion stacked on the second surface of the sensing portion and comprising one or more second base layers containing the second material as a main component, and when observed in the stacking direction, a total thickness of the one or more second base layers in a stacking direction of the sensing portion, the first portion and the second portion is not less than 80% but not more than 120% of a total thickness of the one or more first base layers. In a preferred embodiment, in at least a part of the detection element, the one or more first base layers of the first portion and the one or more second base layers of the second portion are symmetrically located with respect to the sensing portion in the stacking direction.

In the above first aspect, the first base layer and the second base layer are formed of the same main component, and the thickness of the first base layer is substantially equal to the thickness of the second base layer (that is, the total thickness of the one or more second base layers is not less than 80% but not more than 120% of the total thickness of the one or more first base layers). At least a part of the detection element is provided with a symmetrical structure in the stacking direction, along which the first base layer and the second base layer are stacked, the sensing portion being located as a center. Therefore, since stress resulting from a difference in sintering shrinkage is made nearly uniform (symmetrical) in the stacking direction centering around the solid electrolyte layer, warping hardly occurs when sintering. Accordingly, warping of the entire element can be prevented. Therefore, when mounting other members to the detection element, the detection element is hardly subject to cracking or breakage, which can improve assembly performance when producing the gas sensor, and a highly reliable gas sensor can be provided.

The "sensing portion" may partially extend over the detection element or extend over the entire area of the detection element in a direction orthogonal to the stacking direction of the respective layers. Further, the "first portion" and the "second portion" may also partially extend over the area of the detection element or may extend over the detection element in a direction orthogonal to the stacking direction of the respective layers.

Also, each of the sensing portions, the first portion and the second portion may be arranged so as to extend over an entire area of the detection element in a direction orthogonal to the stacking direction. That is, the sensing portion, the first portion and the second portion are stacked at all parts of the detection element. In this manner, a structure in which the three layers, i.e., the solid electrolyte layer that configures the sensing portion, the first base layer that configures the first portion and the second base layer that configures the second portion, are stacked can be formed over a wide region. For this reason, warping of the detection element hardly occurs. Therefore, a gas sensor having greater reliability can be provided.

Further, the second portion of the gas sensor may include an embedded heater element that generates heat by energization.

Accordingly, the heater element for generating heat by energization is embedded in the second portion so as to heat the sensing portion. Therefore, the sensing portion (the solid electrolyte layer) can be efficiently heated.

The sensing portion may include, as the solid electrolyte layer, a first solid electrolyte layer having a first surface and a second solid electrolyte layer having a second surface, wherein the thickness of the second solid electrolyte layer is not less than 80% but not more than 120% of the thickness of the first solid electrolyte layer.

Accordingly, in a preferred embodiment, the sensing portion includes, as the solid electrolyte layer, a first solid electrolyte layer having a first surface and a second solid electrolyte layer having a second surface, and the thickness of the first solid electrolyte layer is substantially equal to the thickness of the second solid electrolyte layer (that is, the thickness of the second solid electrolyte layer is not less than 80% but not more than 120% of the thickness of the first solid electrolyte layer). Therefore, stress produced between the first solid electrolyte layer and the first base layer of the first portion can be made equal to stress produced between the second solid electrolyte layer and the second base layer of the second portion upon sintering. Therefore, the detection element is subject to less warping, whereby the detection element is hardly subject to cracking or breakage when mounting other members to the detection element. Such a configuration improves assembly performance when producing the gas sensor. Further, a highly reliable gas sensor can be provided.

In addition, the solid electrolyte layer may be formed of zirconia as the main component, and the first base layer and the second base layers may be formed of alumina as the main component.

Accordingly, since the solid electrolyte layer adopts zirconia as the main component, detection performance of a specified gas component can be improved. On the other hand, since the first base layer and the second base layer adopt alumina as the main component, durability of the detection element against high temperatures can be improved.

According to a second aspect, the present invention provides a stacking type gas sensor including a plate-shaped detection element formed by simultaneously sintering a plurality of layers stacked on one another and configured to detect a specified gas component in a gas to be detected. The detection element includes: a sensing portion configured to detect the specified gas component and having a first surface and a second surface opposite the first surface, the sensing portion comprising one or more solid electrolyte layers containing a first material as a main component; a porous layer stacked on the first surface of the sensing portion and configured to expose the gas to be measured to the sensing portion; a third base layer stacked on the porous layer on a side opposite the sensing portion in a stacking direction and containing a second material different from the first material as a main component; an introduction hole forming layer stacked on the second surface of the sensing portion and having an atmospheric introduction hole configured to expose the sensing portion to atmospheric gas; and a fourth base layer stacked on the introduction hole forming layer on a side opposite the sensing portion in the stacking direction and containing a third material different from the first material as a main component; and wherein a total thickness of the fourth base layer in a stacking direction of the sensing portion, porous layer, the third base layer, the introduction hole forming layer and the fourth base layer is 80% or more but 120% or less of the total thickness of the third base layer. In a preferred embodiment of the second aspect, in at least a part of the detection element, the third base layer and the fourth base layer are symmetrically located with respect to the sensing portion in the stacking direction.

According to the second aspect of the invention, the third base layer and the fourth base layer are formed of the same main component, and the thickness of the third base layer is substantially equal to that of the fourth base layer (that is, the total thickness of the fourth base layer is 80% or more by 120% or less of the total thickness of the third base layer). In at least a part of the detection element, the third base layer and the fourth base layer are overlap and are symmetrically located with respect to the sensing portion in the stacking direction. Therefore, since stress resulting from a difference in sintering shrinkage is nearly uniform (symmetrical) in the stacking direction centering around the solid electrolyte layer, warping hardly occurs when sintering. Therefore, warping of the entire element can be prevented. In particular, it is possible to prevent cracking in the detection element during sintering due to stress resulting from a difference in sintering shrinkage, which is apt to occur in a structure having a porous layer and an atmospheric introduction hole at both surfaces of the sensing portion. Accordingly, when sintering or when mounting other members to the detection element, the detection element is hardly subject to cracking or breakage. Thus, assembly performance can be improved when producing the gas sensor, and a highly reliable gas sensor can be provided.

The fourth layer of the gas sensor may include an embedded heater element that generates heat by energization.

Accordingly, a heater element that generates heat by energization is embedded in the fourth base layer so as to heat the sensing portion. Therefore, the sensing portion (the solid electrolyte layer) can be efficiently heated.

DETAILED DESCRIPTION OF THE PREFERRED EMBODIMENTS

Embodiments of the present invention are described with reference to the drawings. However, the present invention should not be construed as being limited thereto.

Embodiment 1

Figure 1:
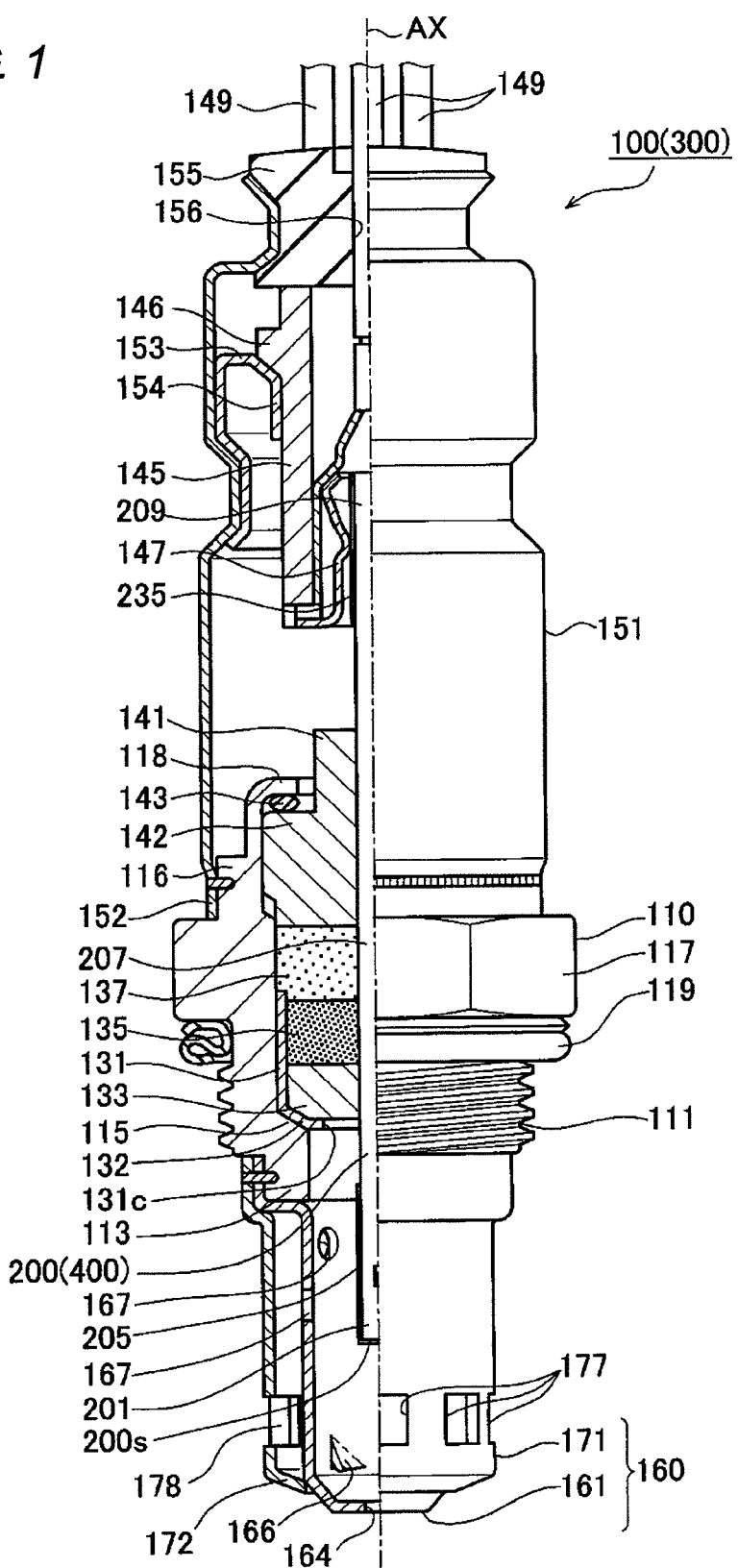
FIG. 1 is a partially sectional view showing a gas sensor according to Embodiment 1.
Figure 2:
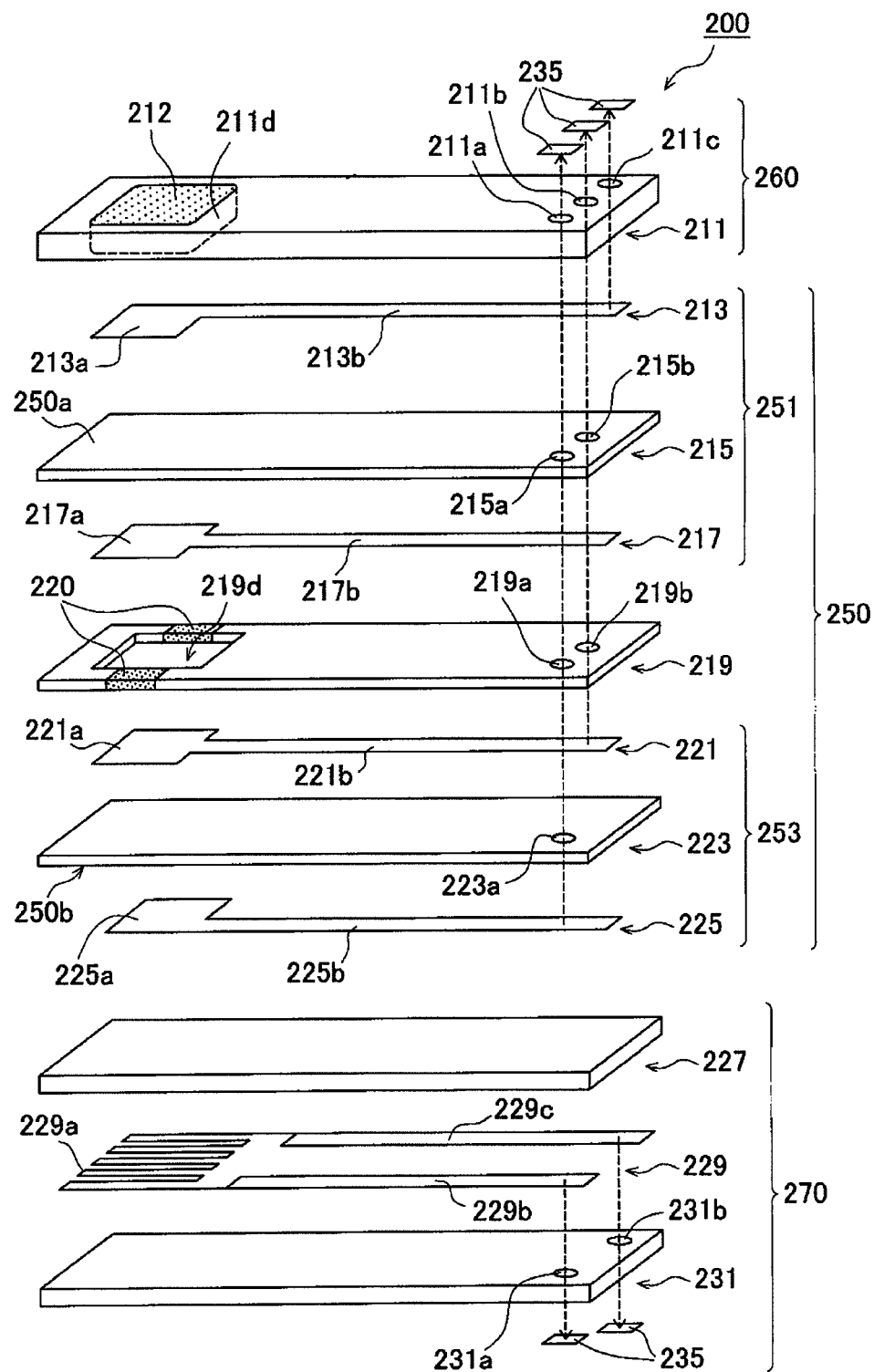
FIG. 2 is a disassembled perspective view showing a detection element of the gas sensor according to Embodiment 1.
Figure 3:
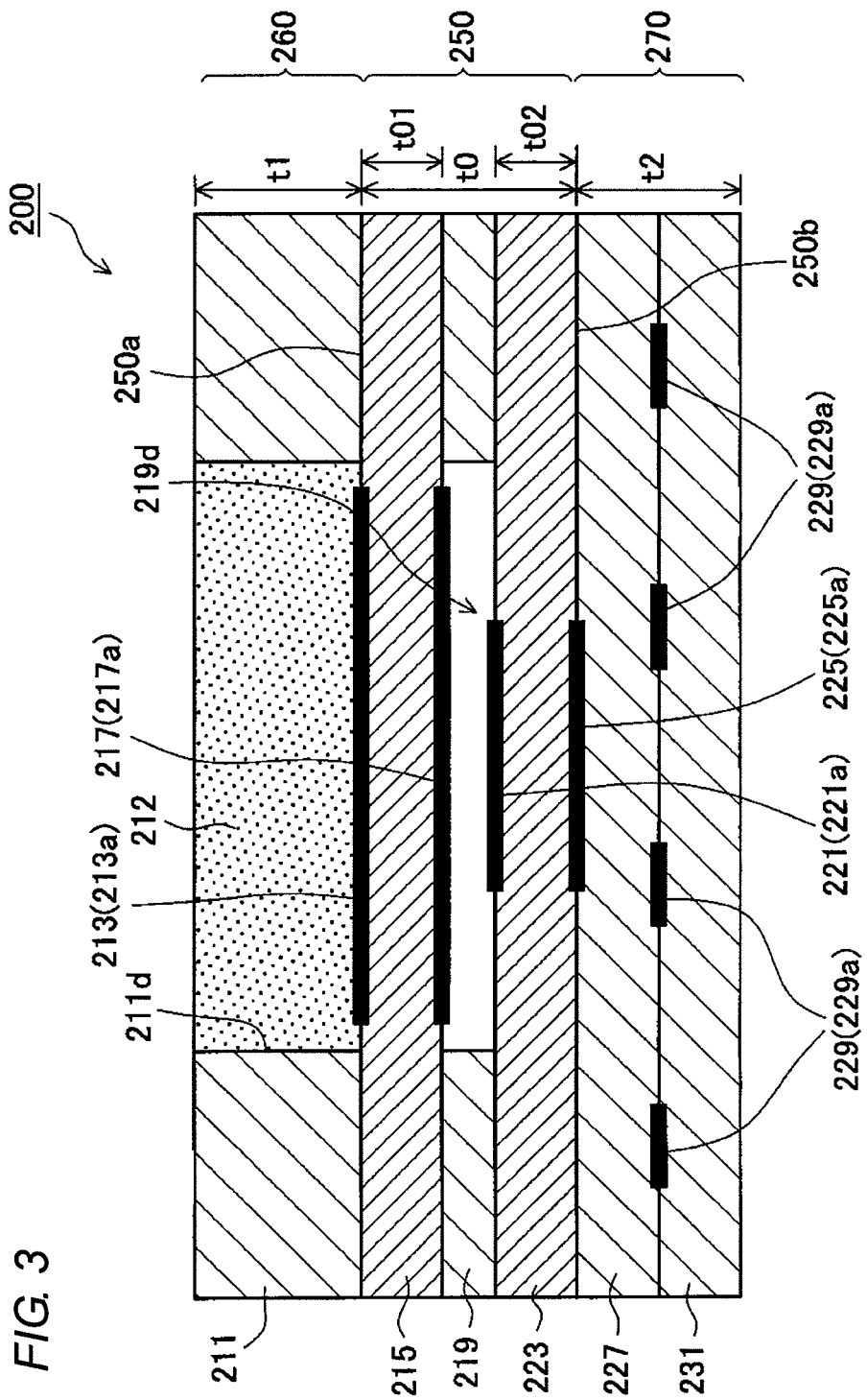
FIG. 3 is a cross-sectional view showing the leading end side portion of the detection element of the gas sensor according to Embodiment 1.
Figure 4:
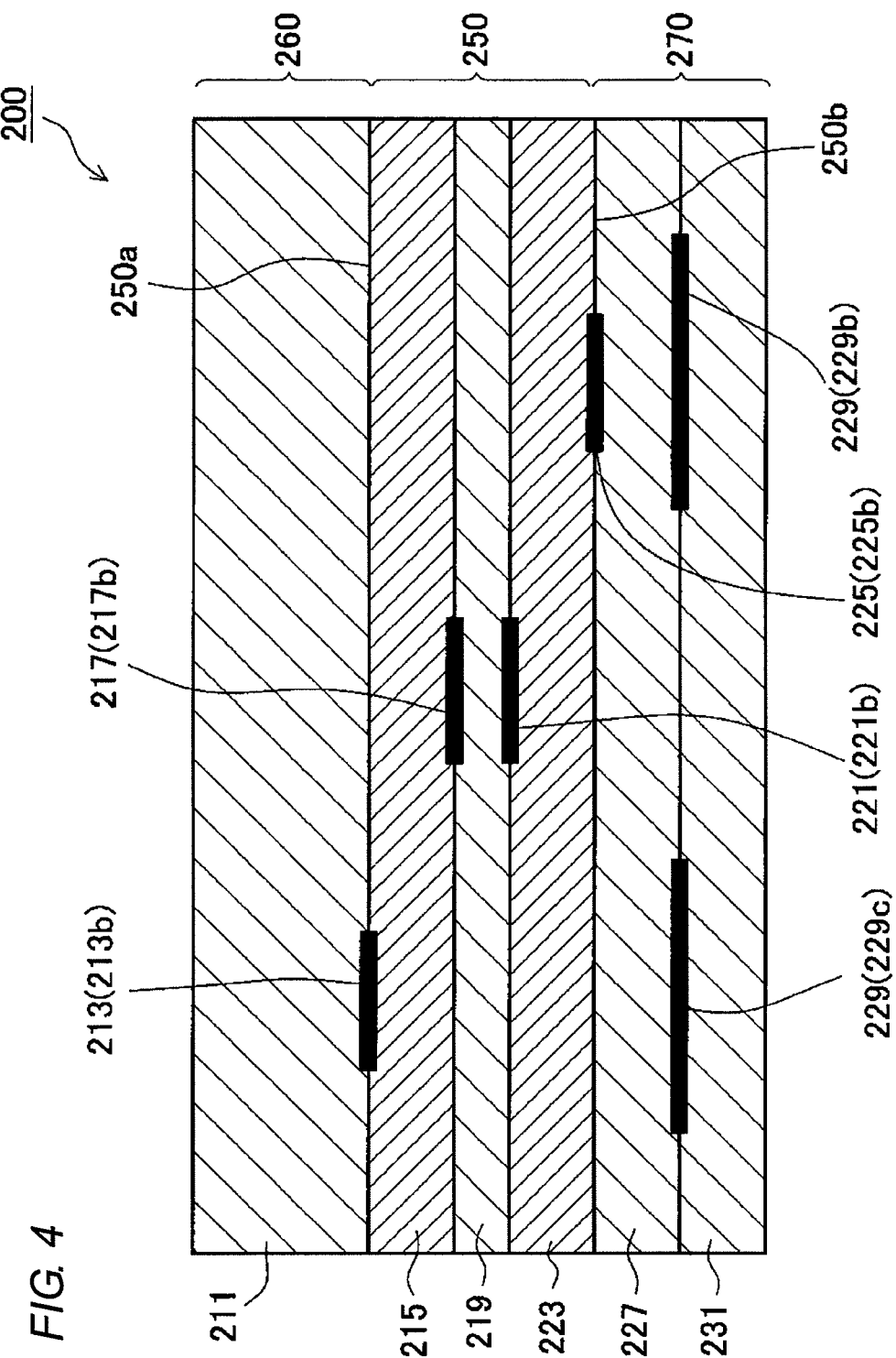
FIG. 4 is a cross-sectional view showing the base end side portion of the detection element of the gas sensor according to Embodiment 1.

Hereinafter, a description is given of an embodiment of the present invention with reference to the drawings. FIG. 1 shows a gas sensor 100 according to Embodiment 1. Also, FIG. 2 is a disassembled perspective view showing a detection element 200 of the gas sensor 100. Further, FIG. 3 and FIG. 4 are cross-sectional views showing the leading end side portion and the base end side portion of the detection element 200, respectively. Also, in FIG. 1, the lower side of the drawing is the leading end side in the axial line AX direction (hereinafter also called a "leading end side"), and the upper side of the drawing is the base end side in the axial line AX direction (hereinafter simply called a "base end side"). Further, in FIG. 2, the left side of the drawing is the leading end side, and the right side of the drawing is the base end side.

The embodiment shows, as an example of the gas sensor 100, a full-range air-fuel ratio sensor attachable to an exhaust pipe of an automobile (not illustrated). The gas sensor 100 measures the air-fuel ratio of exhaust gas based on the concentration of oxygen (specified gas constituent) contained in the exhaust gas. In the embodiment, a detection portion 201 of the detection element 200 is held in the interior of the exhaust pipe and exposed to exhaust gas (the gas to be detected) flowing in the exhaust pipe. The gas sensor 100 includes, as shown in FIG. 1, a cylindrical metal shell 110 extending in the axial line AX direction, a plate-shaped detection element 200 attached to the inside of the metal shell 110, an outer cylinder 151 secured and fixed at the base end side of the metal shell 110, and a protector 160 secured and fixed at the leading end side of the metal shell 110.

Among the components, the detection element 200 has a plate (strip) shape extending in the axial line AX direction (Refer to FIG. 1 through FIG. 4). The leading end portion of the detection element 200 includes the detection portion 201 for detecting an oxygen gas component of the exhaust gas (Refer to FIG. 1). A detection portion protection layer 205 is coated to cover the outer surface of the detection portion 201 and thereby protect it from toxicity of the exhaust gas (Refer to FIG. 1. The detection portion protection layer is omitted in FIG. 2 through FIG. 4).

Five electrode pads 235 (only one of them is illustrated in FIG. 1) are secured on the front surface and the rear surface of the base end portion 209 of the detection element 200. Five connection terminals 147 disposed between the detection element 200 and a separator 145 described below are resiliently brought into contact with and are electrically connected to the electrode pads 235.

As shown in FIGS. 2 through 4, the detection element 200 is formed by simultaneously sintering a plurality of mutually stacked layers containing different main components, and is provided with a plate-shaped sensing portion 250 that has a function of detecting a specified gas component, a plate-shaped protection portion 260 for protecting the sensing portion 250, and a plate-shaped heater portion 270 for heating and activating the sensing portion 250. The protection portion 260 is stacked on one main surface (the first surface 250a) of the sensing portion 250, and the heater portion 270 is stacked on the other main surface (the second surface 250b) of the sensing portion 250. Also, in Embodiment 1, the sensing portion 250 corresponds to the sensing portion of the above aspects of the present invention, the protection portion 260 corresponds to the first portion of the above aspects of the present invention, and the heater portion 270 corresponds to the second portion of the above aspects of the present invention. In this embodiment, the "main component" contained in a layer means a component contained in an amount of 50 wt % or more in the layer.

First, a description is given of the sensing portion 250. The sensing portion 250 includes an oxygen pump cell 251 that forms the first surface 250a, an oxygen concentration detection cell 253 that forms the second surface 250b, and a dense insulating layer 219 stacked therebetween.

The oxygen pump cell 251 includes a dense first solid electrolyte layer 215 having the first surface 250a and the first electrode 213 and the second electrode 217, which are formed on both surfaces of the first solid electrolyte layer 215. The first solid electrolyte layer 215 includes a partially stabilized zirconia sintered body containing zirconia as a main component and having yttria and calcia doped as stabilizing agents. The thickness t01 (Refer to FIG. 3) of the first solid electrolyte layer 215 is 0.2 mm. The first through hole conductor 215a and the second through hole conductor 215b are formed at predetermined positions at the base end side of the first solid electrolyte layer 215 so as to pass therethrough.

The first electrode 213 adopts platinum as a main component and includes the first electrode portion 213a that is formed at a predetermined position at the leading end side and is rectangular in its plan view, and the first lead portion 213b extending from the first electrode portion 213a to the base end side. The first lead portion 213b is electrically connected to the eighth through hole conductor 211c secured at a protection main body layer 211 described below at the base end.

The second electrode 217 adopts platinum as a main component, and includes the second electrode portion 217a, which is formed at a predetermined position at the leading end side and is rectangular in its plan view, and the second lead portion 217b extending from the second electrode portion 217a to the base end side. The second lead portion 217b is electrically connected to the second through hole conductor 215b secured at the first solid electrolyte layer 215 at the base end thereof, and is electrically connected to the fifth through hole conductor 219b secured at an insulating layer 219 described below.

The oxygen concentration detection cell 253 includes a dense second solid electrolyte layer 223 having the second surface 250b, and the third electrode 221 and the fourth electrode 225, which are formed on both surfaces of the second solid electrolyte layer 223. The second solid electrolyte layer 223 includes a partially stabilized zirconia sintered body containing zirconia as the main component and having yttria and calcia doped as stabilizing agents as in the first solid electrolyte layer 215. The thickness t02 (Refer to FIG. 3) of the second solid electrolyte layer 223 is 0.2 mm. Therefore, the thickness t02 of the second solid electrolyte layer 223 is 80% or more but 120% or less of the thickness t01 of the first solid electrolyte layer 215. In this embodiment, the thickness t02 of the second solid electrolyte layer 223 is equal to the thickness t01 of the first solid electrolyte layer 215 (t01=t02). Also, the third through hole conductor 223a is formed at a predetermined position at the base end side of the second solid electrolyte layer 223 so as to pass therethrough.

The third electrode 221 adopts platinum as a main component, and includes the third electrode portion 221a, which is formed at a predetermined position at the leading end side and is rectangular in its plan view, and the third lead portion 221b extending from the third electrode portion 221a to the base end side. The third lead portion 221b is electrically connected to the fifth through hole conductor 219b secured at an insulating layer 219 described below at the base end thereof.

The fourth electrode 225 adopts platinum as the main component and includes the fourth electrode portion 225a, which is formed at a predetermined position at the leading end side thereof and is rectangular in its plan view, and the fourth lead portion 225b extending from the fourth electrode portion 225a to the base end side. The fourth lead portion 225b is electrically connected to the second through hole conductor 223a secured at the second solid electrolyte layer 223 at the base end thereof.

The insulating layer 219 is formed from alumina as a main component. The insulating layer 219 is 0.1 mm thick. Therefore, the entire thickness t0 (Refer to FIG. 3) of the sensing portion 250 is 0.5 mm.

In the insulating layer 219, a gas detection chamber 219d that passes through the insulating layer 219 and is rectangular in its plan view is provided at the position corresponding to the second electrode portion 217a and the third electrode portion 221a. Also, diffusion rate controlling portions 220 that realize gas diffusion between the outside-element portion and the gas detection chamber 219d under a predetermined rate-determining condition are, respectively, provided at both sides in the width direction of the gas detection chamber 219d. The diffusion rate controlling portions 220 include a porous body of alumina.

In addition, the fourth through hole conductor 219a and the fifth through hole conductor 219b are formed at predetermined positions at the base end side of the insulating layer 219 so as to pass therethrough. The fourth through hole conductor 219a is electrically connected to the first through hole conductor 215a secured at the first solid electrolyte layer 215, and is electrically connected to the third through hole conductor 223a secured at the second solid electrolyte layer 223. In addition, the fifth through hole conductor 219b is electrically connected to the second lead portion 217b of the second electrode 217, and is electrically connected to the third lead portion 221b of the third electrode 221.

Next, a description is given of the protection portion 260. The protection portion 260 has a single dense protection main body layer (the first base layer) 211. The protection main body layer 211 includes a material, the main component of which is alumina. The thickness t1 (Refer to FIG. 3) of the protection main body layer 211, that is, the thickness t1 of the protection portion 260 is 0.4 mm.

In the protection main body layer 211, an opening 211d that passes through the protection main body layer 211 and is rectangular in plan view is provided at a position corresponding to the first electrode portion 213a. A porous gas introduction portion 212 the main component of which is alumina is provided in the opening 211d so as to close the opening 211d.

Also, three electrode pads 235 are juxtaposed in the width direction and are disposed at predetermined positions, at the base end side, of the surface of the protection main body layer 211. Further, the sixth through hole conductor 211a, the seventh through hole conductor 211b and the eighth through hole conductor 211c are formed at predetermined positions at the base end side of the protection main body layer 211 so as to pass therethrough. The sixth through hole conductor 211a is electrically connected to one of the electrode pads 235, and is electrically connected to the first through hole conductor 215a secured at the first solid electrolyte layer 215. Further, the seventh through hole conductor 211b is electrically connected to one of the electrode pads 235, and is electrically connected to the second through hole conductor 215b secured at the first solid electrolyte layer 215. Also, the eighth through hole conductor 211c is electrically connected to one of the electrode pads 235, and is electrically connected to the first lead portion 213b of the first electrode 213.

Next, a description is given of the heater portion 270. The heater portion 270 includes a dense first heater insulating layer (the second base layer) 227 having an electrical insulating property, a dense second heater insulating layer (the second base layer) 231 having an electrical insulating property, and a heater element (heater resistor) 229 that is placed therebetween and generates heat by energization. The first heater insulating layer 227 is formed of a material the main component of which is alumina, and is stacked on the second surface 250b of the sensing portion 250. Also, the second heater insulating layer 231 is formed of a material the main component of which is alumina. Since the thickness of the first heater insulating layer 227 is 0.2 mm, and the thickness of the second heater insulating layer 231 is 0.2 mm, the thickness t2 (Refer to FIG. 3) of the thicknesses of the layers 227 and 231, that is, the thickness t2 of the heater portion 270 is 0.4 mm. Therefore, the total thickness t2 of the first and the second heater insulating layers 227 and 231 is 80% or more but 120% or less of the thickness t1 of the protection main body layer 211. In this embodiment, the total thickness t2 of the first and the second heater insulating layers 227 and 231 is equal to the thickness t1 of the protection main body layer 211 (t1=t2).

The ninth through hole conductor 231a and the tenth through hole conductor 231b are formed at predetermined positions at the base end side of the second heater insulating layer 231 so as to pass therethrough. Also, two electrode pads 235 are juxtaposed in the width direction and disposed at predetermined positions at the base end side of the surface of the second heater insulating layer 231. One electrode pad 235 is electrically connected to the ninth through hole 231a, and the other electrode pad 235 is electrically connected to the tenth through hole conductor 231b.

The heater element 229 is arranged at a predetermined position at the leading end side, and includes a meandering heater element 229a having a comb shape, the first heater lead portion 229b extending from one end of the heater portion 229a to the base end side, and the second heater lead portion 229c extending from the other end of the heater portion 229a to the base end side. The first heater lead portion 229b is electrically connected to the ninth through hole conductor 231a secured at the second heater insulating layer 231 at the base end thereof. In addition, the second heater lead portion 229c is electrically connected to the tenth through hole conductor 231b secured at the second heater insulating layer 231 at the base end thereof.

Thus, the detection element 200 according to Embodiment 1 is provided with the sensing portion 250, the main component of which is zirconia, having the first and the second solid electrolyte layers 215 and 223 that function to detect a specified gas component. Also, a protection portion 260, the main component of which is different from that of the first and the second solid electrolyte layers 215 and 223 (in this embodiment, alumina is used as the main component), having a dense protection main body layer 211 is stacked on the first surface 250a of the sensing portion 250. Further, a heater portion 270, the main component of which is the same (in this embodiment, the main component is alumina) as that of the protection main body layer 211, having dense first and second heater insulating layers 227 and 231 is stacked on the second surface 250b of the sensing portion 250.

The total thickness t2 of the first and the second heater insulating layers 227 and 231 is 80% or more but 120% or less of the thickness t1 of the protection main body layer 211. In this embodiment, the total thickness t2 of the first and the second heater insulating layers 227 and 231 is equal to the thickness t1 of the protection main body layer 211 (t1=t2).

Furthermore, the thickness t02 of the second solid electrolyte layer 223 that includes the sensing portion 250 is 80% or more but 120% or less of the thickness t01 of the first solid electrolyte layer 215. In this embodiment, the thickness t02 of the second solid electrolyte layer 223 is equal to the thickness t01 of the first solid electrolyte layer 215 (t01=t02).

Therefore, all the portions excluding the portion having the gas introduction portion 212 provided therein and the portion having the first through the tenth through hole conductors 211a, 211b, 211c, etc., provided therein of the detection element 200 assume a symmetrical structure in which the protection main body layer 211 of the protection portion 260 and the first and the second heater insulating layers 227 and 231 of the heater portion 270 are stacked on one another in a state where the first and the second solid electrolyte layers 215 and 223 of the sensing portion 250 are arranged therebetween.

Next, a description is given of a method for producing the detection element 200. Also, sintered members and unsintered members corresponding thereto will be explained using the same reference numerals for convenience (Refer to FIG. 2).

First, a slurry is prepared, in which a first raw material powder containing alumina powder in an amount of 97 wt % and silica in an amount of 3 wt %, which operates as a sintering adjustment agent, and a plasticizing agent containing butyral resin and dibutyl phthalate (DBP) are dispersed by wet blending. After the slurry is molded into a sheet by a sheet molding method using a doctor blade apparatus, the sheet-like material is cut to a predetermined size, and an unsintered insulating layer 219 corresponding to the insulating layer 219, an unsintered protection main body layer 211 corresponding to the protection main body layer 211, an unsintered first heater insulating layer 227 corresponding to the first heater insulating layer 227, and an unsintered second heater insulating layer 231 corresponding to the second heater insulating layer 231 are formed respectively. Further, the gas detection chamber 219d is formed in the unsintered insulating layer 219. Still further, the opening 211d is formed in the unsintered protection main body layer 211.

Also, a second slurry is prepared, in which a second raw material powder containing alumina powder in an amount of 63 wt % and silica in an amount of 3 wt %, which serves as a sintering adjustment agent, and carbon powder in an amount of 34 wt %, and a plasticizing agent containing butyral resin and DBP are dispersed by wet blending. An unsintered gas introduction portion 212 corresponding to the gas introduction portion 212 is prepared from the slurry.

Also, a third slurry is prepared in which alumina powder (100 wt %) and a plasticizing agent containing butyral resin and DBP are dispersed by wet blending. Unsintered diffusion rate controlling portions 220 corresponding to the diffusion rate controlling portions 220 are prepared using the slurry.

In addition, a fourth slurry is prepared, in which a third raw material powder containing zirconia powder in an amount of 97 wt % and silica ($SiO_2$ powder and alumina powder in a total amount of 3 wt %) operating as a sintering adjustment agent, and a plasticizing agent containing butyral resin and DBP are dispersed by wet blending. An unsintered first solid electrolyte layer 215 corresponding to the first solid electrolyte layer 215 and an unsintered second solid electrolyte layer 223 corresponding to the second solid electrolyte layer 223 are formed using the slurry.

In the order shown from below in FIG. 2, an unsintered second heater insulating layer 231, an unsintered heater element 229 corresponding to the heater element 229, an unsintered first heater insulating layer 227, an unsintered fourth electrode 225 corresponding to the fourth electrode 225, an unsintered second solid electrolyte layer 223, an unsintered third electrode 221 corresponding to the third electrode, an unsintered insulating layer 219, an unsintered second electrode 217 corresponding to the second electrode 217, an unsintered first solid electrolyte layer 215, an unsintered first electrode 213 corresponding to the first electrode 213, and an unsintered protection main body layer 211, etc., are stacked to form an unsintered stacked body.

Specifically, the unsintered heater element 229 is formed on the unsintered second heater insulating layer 231 by screen printing using paste the main component of which is platinum. The unsintered first heater insulating layer 227 is stacked on the unsintered second heater insulating layer 231 and the unsintered heater element 229.

In addition, an unsintered fourth electrode 225 is formed on one surface of the unsintered second solid electrolyte layer 223 by screen printing using a platinum paste containing platinum in an amount of 990 wt % and zirconia powder in an amount of 10 wt %. These are stacked on the unsintered first heater insulating layer 227 so that the unsintered fourth electrode 225 is arranged therebetween. After that, the unsintered third electrode 221 is formed on the unsintered second solid electrolyte layer 223 by screen printing using platinum powder containing platinum in an amount of 90 wt % and zirconia powder in an amount of 10 wt %.

Next, the unsintered insulating layer 219 and the unsintered diffusion rate controlling portions 220 are stacked on the unsintered second solid electrolyte layer 223 and the unsintered third electrode 221. Also, a paste, the main component of which is carbon, is printed on the portion that will become a gas detection chamber 219d after sintering.

Further, the unsintered second electrode 217 is formed on one surface of the unsintered first solid electrolyte layer 215 by screen printing using a platinum paste containing platinum in an amount of 90 wt % and zirconia powder in an amount of 10 wt %. These are stacked on the unsintered insulating layer 219 so that the unsintered second electrode 217 is arranged therebetween. After that, the unsintered first electrode 213 is formed on the unsintered first solid electrolyte layer 215 by screen printing using a platinum paste containing platinum in an amount of 90 wt % and zirconia powder in an amount of 10 wt %.

Next, the unsintered protection main body layer 211 is stacked on the unsintered first solid electrolyte layer 215 and the unsintered first electrode 213. The unsintered gas introduction portion 212 corresponding to the gas introduction portion 212 is formed in advance on the unsintered protection main body layer 211. Thus, the unsintered stacked body is formed.

Next, after the unsintered stacked body is pressed and pressure-fitted at 1 MPa, it is cut to a predetermined size. After that, resin is removed from the unsintered stacked body, and the assembly is subjected to regular sintering at 1500° C. for one hour, thereby obtaining a detection element 200.

After that, an unsintered detection portion protection layer 205 corresponding to the detection portion protection layer 205 is formed on the periphery at the leading end portion 201 of the detection element 200 using a slurry of spinel powder, titanium and alumina sol. Thereafter, the detection element 200 is heat treated at a sintering temperature of 1000° C. for three hours, thereby obtaining a detection element 200 having the detection portion protection layer 205.

Next, a description is given of other parts of the gas sensor 100. A cylindrical metallic cup 131 having a bottom is disposed at a slightly leading end side from the middle of the barrel portion 207 of the detection element 200 so that the detection element 200 is inserted thereinto and the detection portion 201 thereof protrudes from the opening having a cylindrical bottom 131c. The metallic cup 131 holds the detection element 200 in the metal shell 110, and the leading end circumferential edge portion 132 is tapered so that the diameter thereof decreases toward the leading end side. An alumina-made ceramic ring 133 and a first talc ring 135 of compressed talc powder are accommodated in the metallic cup 131 so that the detection element 200 is inserted thereinto. The first talc ring 135 is crushed in the metallic cup 131 and is thoroughly filled therein, whereby the detection element 200 is positioned and held in the metallic cup 131.

The detection element 200 integrated with the metallic cup 131 is held with the periphery in the diametrical direction thereof surrounded by the cylindrical metal shell 110. The metal shell 110 is adapted to attach and fix the gas sensor 100 to an exhaust pipe of an automobile, and is made of a low-carbon steel such as SUS430. A male-threaded portion 111 is formed at the leading end side of the outer circumference of the metal shell 110 for attaching to the exhaust pipe. Also, at a further leading end side of the male-threaded portion 111, an annular-shaped leading end fixing portion 113 protrudes at which the protector 160 described below is fixed.

In addition, a tool engaging portion 117 with which an attaching tool is engaged is formed at the middle of the outer circumference of the metal shell 110. Also, a gasket 119 for preventing gas from leaking when the metal shell 110 is attached to the exhaust pipe is inserted between the tool engaging portion 117 and the male-threaded portion 111. Further, a base end fixing portion 116 at which an outer cylinder 151 described below is fixed is formed at the base end side of the tool engaging portion 117. Also, at further base end side, a crimping portion 118 for crimping and holding the detection element 200 in the metal shell 110 is formed.

Further, a tapered stepped portion 115 the diameter of which is reduced toward the leading end side is formed at the leading end side of the inner circumference of the metal shell 110. A tapered leading end circumferential edge portion 132 of the metallic cup 131 for holding the detection element 200 is engaged at the stepped portion 115. Further, the second talc ring 137 is disposed at the base end side of the metallic cup 131 inside the metal shell 110 in a state in which the detection element 200 is inserted thereinto. A cylindrical sleeve 141 is fitted in the metal shell 110 with the second talc ring 137 pressed from the base end side. A step-shaped shoulder portion 142 is formed at the sleeve 141. An annular crimping packing 143 is arranged at the shoulder portion 142. The crimping portion 118 of the metal shell 110 is crimped via the crimping packing 143 so as to press the shoulder portion 142 of the sleeve 141 toward the leading end side.

The second talc ring 137 pressed by the sleeve 141 is crushed in the metal shell 110 and thoroughly filled therein. The metallic cup 131 and the detection element 200 are positioned and held in the metal shell 110 by the second talc ring 137 and the first talk ring 135 filled in advance in the metallic cup 131. Airtightness inside the metal shell 110 can be maintained by the crimping packing 143 intervening between the crimping portion 118 and the shoulder portion 142 of the sleeve 141, to thereby prevent combustion gas from flowing out.

In the detection element 200, the base end portion 209 thereof protrudes toward the base end side from the crimping portion 118 which is the base end portion of the metal shell 110, and a cylindrical separator 145 made of insulating ceramic covers the base end portion 209. The separator 145 internally holds five connection terminals 147 (only one thereof is illustrated in FIG. 1) that are electrically connected to five electrode pads 235 formed at the base end portion 209 of the detection element 200. These connection terminals 147 are electrically connected to five lead wires 149 (only three wires thereof are illustrated in FIG. 1) led out from the gas sensor 100. The separator 145 accommodates the connection terminals 147 and the lead wires 149 while insulating the respective connection parts thereof from each other.

The outer cylinder 151 is disposed so as to surround the periphery of the separator 145. The outer cylinder 151 is made of stainless steel (SUS 304 in the embodiment), and a leading end opening portion 152 is disposed outside in the diametrical direction of the base end fixing portion 116 of the metal shell 110. The leading end opening portion 152 is crimped from the outside, laser-welded around the outer circumference, and cemented to the base end fixing portion 116.

Also, a metal-made cylindrical retaining metal fitting 153 is disposed in the clearance between the outer cylinder 151 and the separator 145. The retaining metal fitting 153 has a supporting portion 154 constructed by bending the base end thereof inwardly. The retaining metal fitting 153 supports the separator 145 by engaging a collar portion 146 provided at the outer circumference of the base end side of the separator 145 with supporting portion 154. In this state, the outer cylinder 151 at the portion where the retaining metal fitting 153 is arranged is crimped from the outside, and the retaining metal fitting 153 by which the separator 145 is supported is fixed at the outer cylinder 151.

In addition, a grommet 155 made of fluorine-based rubber is fitted to the base end side opening of the outer cylinder 151. The grommet 155 has five insertion holes 156 (only one thereof is illustrated in FIG. 1), and five lead wires 149 extending from the separator 145 are airtightly inserted into the respective insertion holes 156. In this state, the grommet 155 is crimped from outside the outer cylinder 151 while pressing the separator 145 to the leading end side, and is fixed at the outer cylinder 151.

The detection element 200 held at the metal shell 110 has a detection portion 201 protruding from the leading end fixing portion 113 that is the leading end portion of the metal shell 110. A protector 160 is fitted and fixed by laser welding to the leading end fixing portion 113 in order to protect the detection portion 201 of the detection element 200 from breakage due to contamination and contact with water by deposits (toxic adhered substances such as fuel ash and oil constituents) present in exhaust gas. The protector 160 has a double structure including a cylindrical inside protector 161 having a bottom and an outer protector 171 forming a cylinder, which surrounds the periphery in the diametrical direction of the inside protector 161 via an air gap.

The inside protector 161 forms a cylindrical shape having a bottom and is fixed at the metal shell 110 with the detection portion 201 of the detection element 200 disposed in the interior thereof. A plurality of inside introduction holes 167 for introducing exhaust gas from the exterior thereof into the interior are provided at a further base end side from the leading end 200s of the detection element 200 at the inside protector 161. The inside introduction holes 167 are divided into two stages in the axial line AX direction, and are, respectively, juxtaposed in the circumferential direction. Also, a plurality of (three) water drain holes 166 notched and opened inwardly are juxtaposed and provided in the circumferential direction at the leading end side of the inside protector 161. These water drain holes 166 are at a further leading end side from the leading end 200s of the detection element 200. In addition, an exhaust hole 164 for outwardly exhausting exhaust gas and water is formed at the middle of the bottom wall of the inside protector 161.

On the other hand, the outside protector 171 is fixed at the metal shell 110 so as to surround the periphery in the diametrical direction of the inside protector 161 via an air gap. The leading end portion 172 of the outside protector 171 is bent inside toward the inside protector 161. Therefore, the air gap between the inside protector 161 and the outside protector 171 is closed at the leading end side. Also, a plurality of (eight) outside introduction holes 177 for introducing exhaust gas from the exterior thereof into the interior are juxtaposed in the circumferential direction and formed at a predetermined position at a further leading end side from the leading end 200s of the detection element 200 of the outside protector 171. Plate-shaped guide bodies 178 extending inwardly are provided at the respective outside introduction holes 177. Therefore, exhaust gas introduced from the exterior into the interior via the outside introduction holes 177 produces a swirling flow, by which the exhaust gas swirls in the circumferential direction of the axial line AX, in the air gap to the inside protector 161.

The gas sensor 100 is produced as described above. That is, the detection element 200 that has been produced by the above-described method is inserted into the metallic cup 131, and is fixed with the ceramic ring 133 and the first talc ring 135, thereby forming an assembly. After that, the assembly is inserted into the metal shell 110 to which the protector 160 is cemented, and further the second talc ring 137, the sleeve 141 and the crimping packing 143 are inserted and crimped by the crimping portion 118 of the metal shell 110, thereby forming a lower part assembly. On the other hand, the outer cylinder 151, the separator 141, the grommet 155, etc., are assembled to form an upper part assembly. The lower part assembly and the upper part assembly are attached to each other to complete the gas sensor 100.

As described above, in Embodiment 1, the protection main body layer 211, the first and the second heater insulating layers 227 and 231 are formed of the same main component (in this embodiment, alumina), and the thicknesses thereof are made substantially equal to each other (in this embodiment, the same thickness, that is, $t1=t2$). A symmetrical structure is adopted in which the protection main body layer 211, the first and the second heater insulating layers 227 and 231 symmetrically overlap in their thickness direction centering around the first and the second solid electrolyte layers 215 and 223. Therefore, stress resulting from a difference in sintering shrinkage is nearly uniform (symmetrical) in the thickness direction centering around the first and the second solid electrolyte layers 215 and 223. Consequently, warping hardly occurs, and warping of the entire element can be prevented. Therefore, when attaching other members to the detection element 200, the detection element 200 is hardly subject to cracking or breakage. Thus, assembly performance for producing the gas sensor 100 is improved, and a highly reliable gas sensor 100 can be provided.

In addition, in Embodiment 1, the sensing portion 250, the protection portion 260 and the heater portion 270 are, respectively, arranged entirely in a direction orthogonal to the stacking direction of the respective layers of the detection element 200. That is, the sensing portion 250, the protection portion 260 and the heater portion 270 overlap one another at all parts of the detection element 200. In this manner, an overlapping structure can be formed over a wide range, in which three members of the sensing portion 250, the protection main body layer 211 of the protection portion 260 and the first and the second heater insulating layers 227 and 231 of the heater portion 270 overlap one another. Specifically, in Embodiment 1, all the portions excluding the portion, at which the gas introduction portion 212 is provided, of the detection element 200, and the portion at which the first through the tenth through hole conductors 211a, 211b 211c, etc., form a symmetrical structure. Accordingly, warping hardly occurs when sintering the detection element 200, and a gas sensor 100 of greater reliability can be provided.

Also, in Embodiment 1, the first solid electrolyte layer 215 and the second solid electrolyte layer 225, which includes the sensing portion 250, are made to have the same thickness (in this embodiment, the same thickness, that is, $t01=t02$). Therefore, when sintering, stress produced between the first solid electrolyte layer 215 and the protection main body layer 211 of the protection portion 260 can be made equal to the stress produced between the second solid electrolyte layer 223 and the first and the second heater insulating layers 227, 231 of the heater portion 170. Accordingly, even from this point, when sintering, warping hardly occurs in the detection element 200. Also, when attaching other members to the detection element 200, the detection element 200 is hardly subject to cracking or breakage, wherein assembly performance in producing the gas sensor 100 can be improved, and a highly reliable gas sensor 100 can be provided.

In addition, since the first and the second solid electrolyte layers 215 and 223 employ zirconia as a main component, it is possible to provide good detection performance of a specified gas component. On the other hand, since the protection main body layer 211 and the first and the second heater insulating layers 227 and 231 employ alumina as the main component, durability of the detection element 200 against high temperatures can be improved.

Embodiment 2

Figure 5:
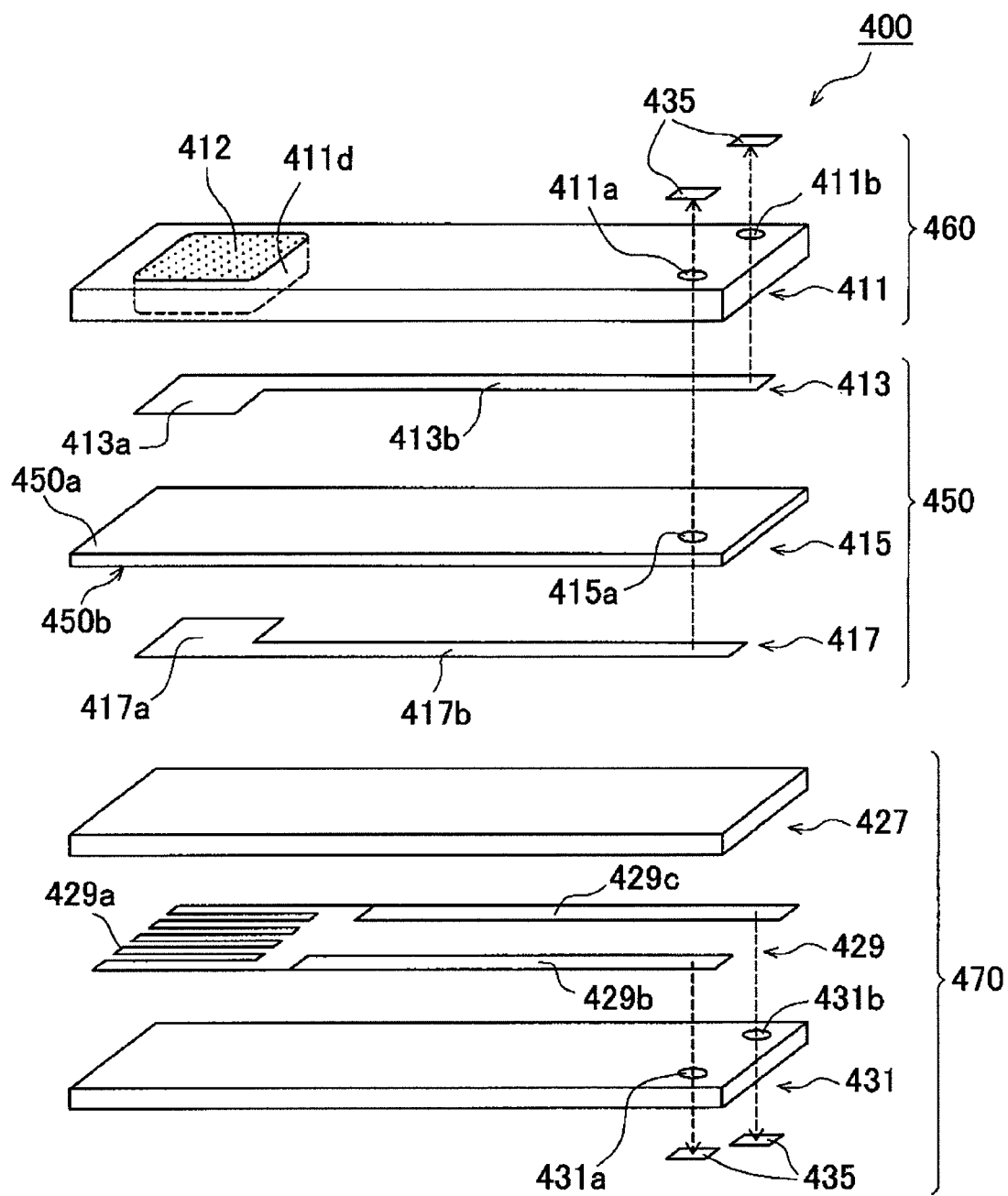
FIG. 5 is a disassembled perspective view showing a detection element of the gas sensor according to Embodiment 2.
Figure 6:
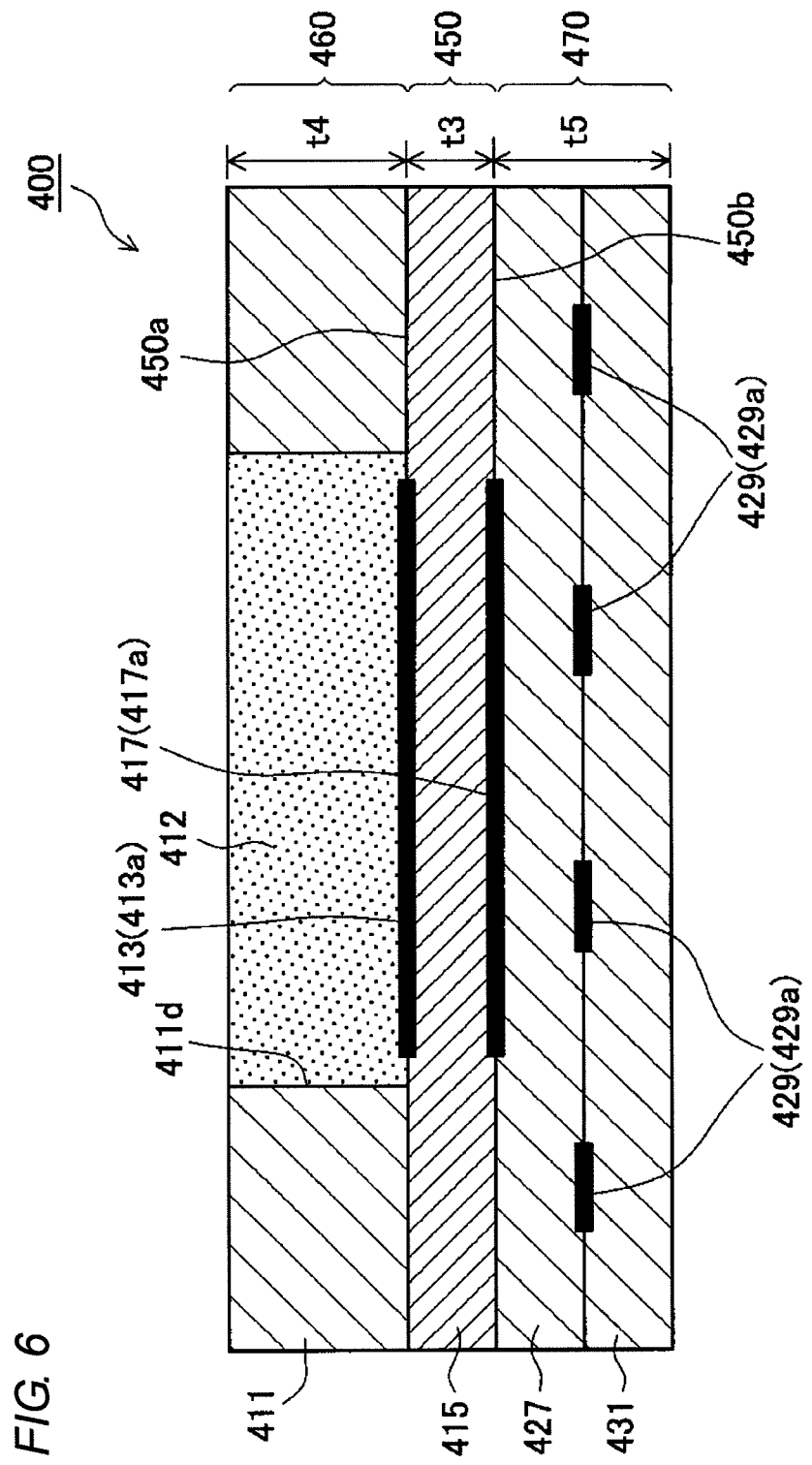
FIG. 6 is a cross-sectional view showing the leading end side portion of the detection element of the gas sensor according to Embodiment 2.
Figure 7:
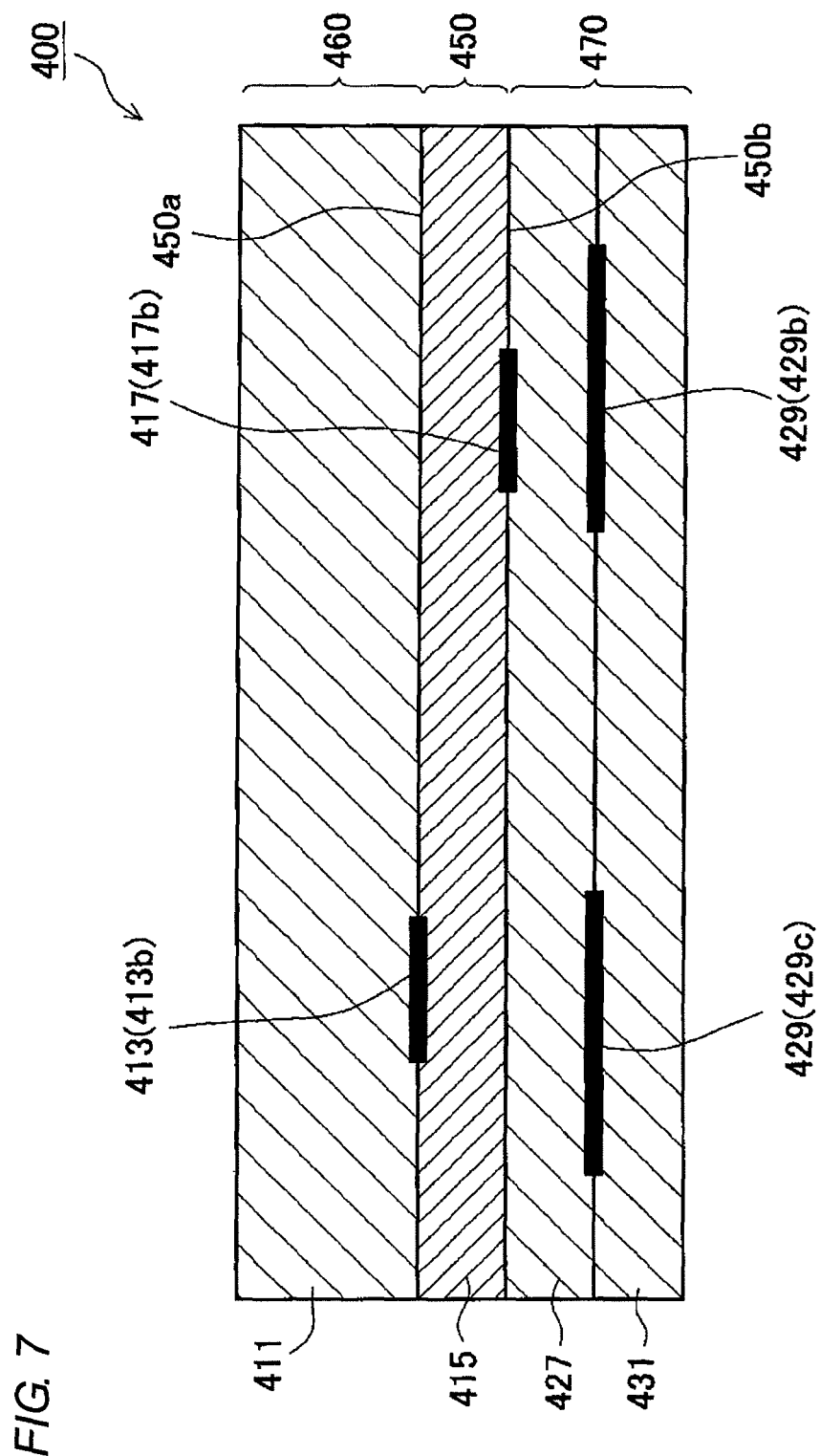
FIG. 7 is a cross-sectional view showing the base end side portion of the detection element of the gas sensor according to Embodiment 2.

Next, a description is given of Embodiment 2. FIG. 5 is a disassembled perspective view of a detection element 400 that includes a gas sensor 300 according to the above aspects of the present invention. Further, FIGS. 6 and 7 are cross-sectional views showing the leading end side portion and the base end side of the detection element 400, respectively. In the gas sensor 300 according to the present embodiment, the mode of the detection element 400 is different from the mode of the detection element 200 of the gas sensor 100 according to Embodiment 1. Other features are basically similar to those of Embodiment 1 described above. Descriptions of parts that are similar to those of Embodiment 1 are omitted or simplified.

The detection element 400 according to Embodiment 2 is formed by simultaneously sintering a plurality of mutually stacked layers containing different main components, and has a plate shape (that is, a plate strip) extending in the axial line AX direction. The detection element 400 includes a sensing portion 450, a protection portion 460 and a heater portion 470. The protection portion 460 is stacked on one main surface (the first surface 450a) of the sensing portion 450, and the heater portion 470 is stacked on the other main surface (the second surface 450b) of the sensing portion 450. Also, the sensing portion 450 corresponds to the sensing portion according to the above aspects of the present invention. The protection portion 460 corresponds to the first portion according to the above aspects of the present invention, and the heater portion 470 corresponds to the second portion according to the above aspects of the present invention.

First, a description is given of the sensing portion 450. The sensing portion 450 includes a dense solid electrolyte layer 415 constituting an oxygen concentration cell and the first electrode 413 and the second electrode 417, which are formed at both surfaces of the solid electrolyte layer 415. The solid electrolyte layer 415 comprises a partially stabilized zirconia sintered body the main component of which is zirconia, and further contains yttria or calcia doped as a stabilizing agent. The thickness t3 (Refer to FIG. 6) of the solid electrolyte layer 415 is 0.5 mm, and the first through hole conductor 415a is formed at a predetermined position of the base end side of the solid electrolyte layer 415 so as to pass therethrough.

The first electrode 413 employs platinum as a main component and includes the first electrode portion 413a formed at a predetermined position at the leading end side, which is rectangular in plan view, and the first lead portion 413b extending from the first electrode portion 413a to the base end side. The first lead portion 413b is electrically connected to the third through hole conductor 411b secured at a protection main body layer 411 described below at the base end thereof.

The second electrode 417 employs platinum as a main component, and includes the second electrode portion 417a formed at a predetermined position at the leading end side, which is rectangular in plan view, and a second lead portion 417b extending from the second electrode portion 417a to the base end side. The second lead portion 417b is electrically connected to the first through hole conductor 415a secured at the solid electrolyte layer 415 at the base end thereof.

Next, a description is given of the protection portion 460. The protection portion 460 has a single dense protection main body layer (the first base layer) 411. The protection main body layer 411 is made of a material the main component of which is alumina. The thickness t4 (Refer to FIG. 6) of the protection main body layer 411, that is, the thickness t4 of the protection portion 460 is 0.5 mm. In addition, an opening 411d that passes through the protection main body layer 411 and is rectangular in plan view is provided at a position corresponding to the first electrode portion 413a at the protection main body layer 411. A porous gas introduction portion 412 the main component of which is alumina is provided in the opening 411d so as to close the opening 411d.

Further, two electrode pads 435 are juxtaposed in the width direction and disposed at a predetermined position at the base end side of the surface of the protection main body layer 411. Further, the second through hole conductor 411a and the third through hole conductor 411b are formed at predetermined positions at the base end side of the protection main body layer 411 so as to pass therethrough. The second through hole conductor 411a is electrically connected to one electrode pad 435, and is electrically connected to the first through hole conductor 415a secured at the solid electrolyte layer 415. In addition, the third through hole conductor 411b is electrically connected to the other electrode pad 435, and is electrically connected to the first lead portion 413b of the first electrode 413.

Next, a description is given of the heater portion 470. The heater portion 470 includes a dense first heater insulating layer 427 (the second base layer) having an electrical insulating property, a dense second heater insulating layer 431 (the second base layer) having an electrical insulating property, and a heater element 429 that generates heat by energization. The heater insulating layer 427 is formed of a material the main component of which is alumina, and is stacked on the second surface 450b of the sensing portion 450. Also, the second heater insulating layer 431 is formed of a material the main component of which is alumina. Since each of the first heater insulating layer 427 and the second heater insulating layer 431 has a thickness of 0.25 mm, the thickness t5 (Refer to FIG. 6) which is the total of the thicknesses of the layers 427 and 431, that is, the thickness t5 of the heater portion 470, is 0.5 mm. Therefore, the total thickness t5 (the thickness t5 of the heater portion 470) of the first and the second heater insulating layers 427 and 431 is equal to the thickness t4 of the protection main body layer 411 (the thickness t4 of the protection portion 460). That is, t4=t5.

Also, the fourth through hole conductor 431a and the fifth through hole conductor 431b are formed at predetermined positions at the base end side of the second heater insulating layer 431 so as to pass therethrough. Further, two electrode pads 435 are juxtaposed in the width direction and are disposed at predetermined positions at the base end side of the second heater insulating layer 431. One electrode pad 435 is electrically connected to the fourth through hole conductor 431a, and the other electrode pad 435 is electrically connected to the fifth through hole conductor 431b.

The heater element 429 includes a zigzag or rather comb-shaped (meandering) heater portion 429a disposed at a predetermined position at the leading end side, the first heater lead portion 429b extending from one end of the heater portion 429a to the base end side, and the second heater lead portion 429c extending from the heater portion 429c to the base end side. The first heater lead portion 429b is electrically connected to the fourth through hole conductor 431a secured at the second heater insulating layer 431 at the base end side thereof. Also, the second heater lead portion 429c is electrically connected to the fifth through hole conductor 431b secured at the second heater insulating layer 431 at the base end thereof.

Thus, the detection element 400 according to Embodiment 2 employs zirconia as a main component and includes a sensing portion 450 having a solid electrolyte layer 415 that functions to detect a specified gas component. Also, the protection portion 460 having a dense protection main body layer 411, the main component of which differs from the main component of the solid electrolyte layer 415 (in this embodiment, alumina is used as the main component), is stacked on the first surface 450a of the sensing portion 450. In addition, the heater portion 470 having dense first and second heater insulating layers 427 and 431, the main component of which is the same as that of the protection main body layer 411 (in this embodiment, alumina is used as the main component), is stacked on the second surface 450b of the sensing portion 450.

Further, the total thickness t5 of the first and the second heater insulating layers 427 and 431 is 80% or more but 120% or less of the thickness t4 of the protection main body layer 411. In this embodiment, the total thickness t5 of the first and the second heater insulating layers 427 and 431 is equal to the thickness t4 of the protection main body layer 411 (that is, t4=t5).

Therefore, all the portions, excluding the portion where the gas introduction portion 412 is provided and the portion where the first through the fifth through hole conductors 411a, 411b, etc., are provided, of the detection element 400 assumes a symmetrical structure. That is, a symmetrical structure is provided, in which three members of the sensing portion 450, the protection main body layer 411 of the protection portion 460, and the first and the second heater insulating layers 427 and 431 of the heater portion 470 symmetrically overlap in the thickness direction.

Next, a description is given of a method for producing the detection element 400. Also, a description is given of sintered members and unsintered members corresponding thereto using the same reference numerals for convenience (Refer to FIG. 5).

First, a slurry is prepared, in which a first raw material powder containing alumina powder in an amount of 97 wt % and silica in an amount of 3 wt %, which operates as a sintering adjustment agent, and a plasticizing agent containing butyral resin and DBP are dispersed by wet blending. An unsintered protection main body layer 411 corresponding to the protection main body layer 411, an unsintered first heater insulating layer 427 corresponding to the first heater insulating layer 427, and an unsintered second heater insulating layer 431 corresponding to the second heater insulating layer 431 are respectively formed from the slurry. Further, an opening 411d is formed in the unsintered protection main body layer 411.

Also, a second slurry is prepared, in which a second raw material powder containing alumina powder in an amount of 63 wt % and silica in an amount of 3 wt % and carbon powder in an amount of 34 wt %, which operate as a sintering adjustment agent, and a plasticizing agent containing butyral resin and DBP are dispersed by wet blending. An unsintered gas introduction portion 412 corresponding to the gas introduction portion 412 is prepared from the slurry.

In addition, a third slurry is prepared, in which a third raw material powder containing zirconia powder in an amount of 97 wt % and silica ($SiO_2$) powder and alumina powder in a total amount of 3 wt %), which operates as a sintering adjustment agent, and a plasticizing agent containing butyral resin and DBP are dispersed by wet blending. An unsintered solid electrolyte layer 415 corresponding to the solid electrolyte layer 415 is formed from the slurry.

In the order shown from below in FIG. 5, an unsintered second heater insulating layer 431, an unsintered heater element 429 corresponding to the heater element 429, the unsintered first heater insulating layer 427, an unsintered second electrode 417 corresponding to the second electrode 417, the unsintered solid electrolyte layer 415, an unsintered first electrode 413 corresponding to the first electrode 413, and the unsintered protection main body layer 411, etc., are stacked, wherein an unsintered stacked body is prepared.

Specifically, the unsintered heater element 429 is formed on the unsintered second heater insulating layer 431 by screen printing using a paste, the main component of which is platinum. The unsintered first heater insulating layer 427 is stacked on the unsintered second heater insulating layer 431 and the unsintered heater element 429.

Also, the unsintered second electrode 417 is formed on the unsintered solid electrolyte layer 415 by screen printing using a platinum paste, containing platinum in an amount of 90 wt % and zirconia in an amount of 10 wt %. These are stacked on the unsintered first heater insulating layer 427 so as to arrange the unsintered second electrode 417 therebetween. After that, the unsintered first electrode 413 is formed on the unsintered solid electrolyte layer 415 by screen printing using platinum paste containing platinum in an amount of 90 wt % and zirconia in an amount of 10 wt %.

Next, the unsintered protection layer 411 is stacked on the unsintered solid electrolyte layer 415 and the unsintered first electrode 413. The unsintered gas introduction portion 412 corresponding to the gas introduction portion 212 is formed in advance in the unsintered protection main body layer 411. Thus, the unsintered stacked body is formed.

Next, after the unsintered stacked body is pressed and pressure-fitted at 1 MPa, it is cut to a predetermined size. After that, resin is removed from the unsintered stacked body, and the assembly is further subjected to regular sintering at 1500° C. for one hour, thereby obtaining a detection element 400.

After that, an unsintered detection portion protection layer corresponding to the detection portion protection layer (not illustrated) is formed on the periphery at the leading end side of the detection element 400 using a slurry of spinel powder, titanium and alumina sol. Thereafter, the detection element 400 is heat treated at a sintering temperature of 1000° C. for three hours, thereby obtaining a detection element 400 having the detection portion protection layer.

Further, in the detection element 400 according to Embodiment 2, the quantity (four) of the electrode pads 435 differs from the quantity (five) of the electrode pads 235 of the detection element 200 according to Embodiment 1. Therefore, members associated with the electrode pads 435, for example, connection terminals 147, lead wires 149, separator 145, etc., (Refer to FIG. 1), constituting the gas sensor 300 differ in terms of the quantity and mode depending on the quantity of the electrode pads 435.

As described above, in Embodiment 2, the protection main body layer 411 and the first and the second heater insulating layers 427 and 431 are formed of the same main component (in this embodiment, alumina), and the thicknesses thereof are made substantially equal to each other (in this embodiment, the same thickness, t4=t5). Further, a symmetrical structure is provided in which the protection main body layer 411, the first and the second heater insulating layers 427 and 431 symmetrically overlap in the thickness direction centering around the solid electrolyte layer 415. Therefore, since stress resulting from a difference in sintering shrinkage is almost evenly (symmetrically) produced in the thickness direction centering around the solid electrolyte layer 415, warping hardly occurs, and it is possible to prevent the entirety of the element from warping. Accordingly, when attaching other members to the detection element 400, the detection element 400 is hardly subject to cracking or breakage. In this manner, assembly performance can be improved when producing the gas sensor 300, and a highly reliable gas sensor 300 can be provided.

Still further, portions similar to those of Embodiment 1 can bring about actions and effects similar to those of Embodiment 1.

Embodiment 3

Figure 8:
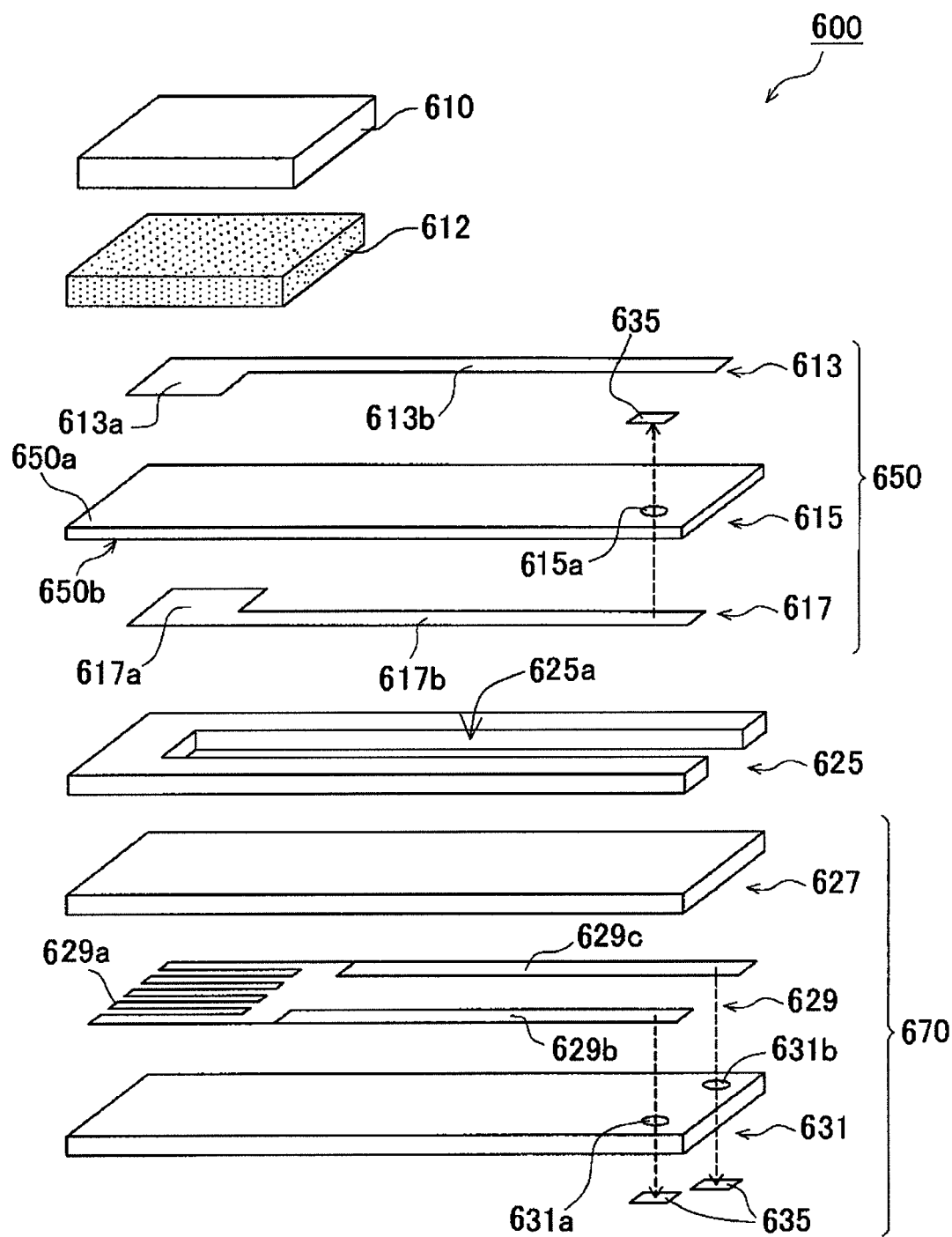
FIG. 8 is a disassembled perspective view showing a detection element of the gas sensor according to Embodiment 3.
Figure 9:
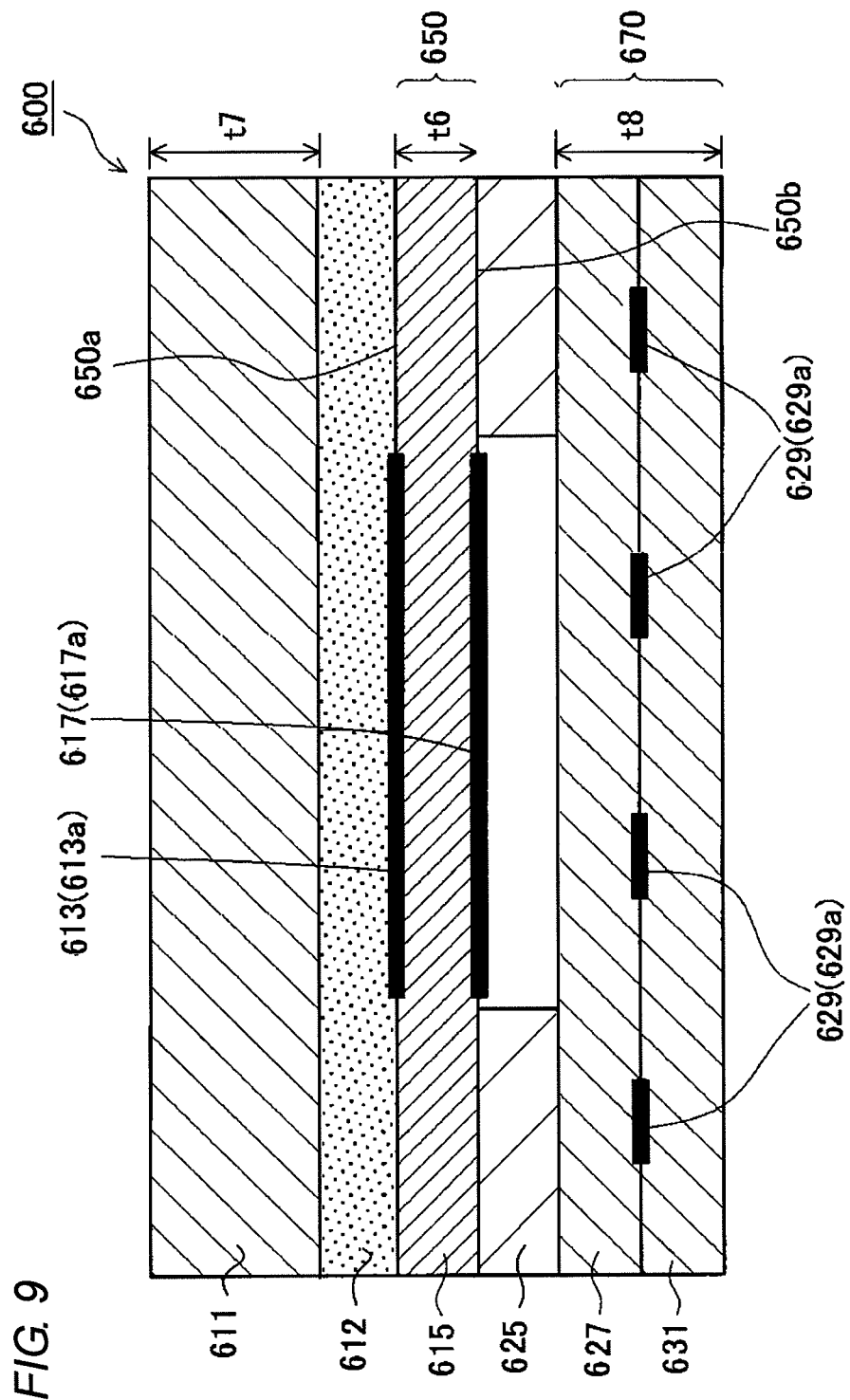
FIG. 9 is a cross-sectional view showing the leading end side portion of the detection element of the gas sensor according to Embodiment 3.

Next, a description is given of Embodiment 3. FIG. 8 is a disassembled perspective view showing a detection element 600 of a gas sensor according to Embodiment 3. Further, FIG. 9 is a cross-sectional view showing the leading end side portion of the detection element 600. In the gas sensor according to Embodiment 3, the mode of the detection element 600 differs from that of the detection element 200 of the gas sensor 100 according to Embodiment 1. Other features are basically similar to those of Embodiment 1 described above, and descriptions of portions similar to those of Embodiment 1 are omitted or simplified.

The detection element 600 according to Embodiment 3 is formed by simultaneously sintering a plurality of mutually stacked layers containing different main components, and has a plate shape (that is, plate strip) extending in the axial line AX direction. The detection element 600 includes a sensing portion 650, a porous layer 612, a shielding layer 610, an introduction hole forming layer 625, and a heater portion 670. The porous layer 612 and the shielding layer 610 are stacked on one main surface (the first surface 650a) of the sensing portion 650, and the introduction hole forming layer 627 and the heater portion 670 are stacked on the other main surface (the second surface 650b) of the sensing portion 650. Also, the shielding layer 610 corresponds to the third base layer of the above aspects of the present invention.

First, a description is given of the sensing portion 650. The sensing portion 650 includes a dense solid electrolyte layer 615 constituting an oxygen concentration cell and the first electrode 613 and the second electrode 617, which are formed at both side of the solid electrolyte layer 615. The solid electrolyte layer 615 comprises a partially stabilized zirconia sintered body the main component of which is zirconia, and further contains yttria or calcia doped as a stabilizing agent. The thickness t6 (Refer to FIG. 9) of the solid electrolyte layer 615 is 0.5 mm, and the first through hole conductor 615a is formed at a predetermined position of the solid electrolyte layer 615 so as to pass therethrough.

The first electrode 613 contains platinum as a main component and includes a first electrode portion 613a formed at a predetermined position at the leading end side, which is rectangular in plan view, and a first lead portion 613b extending from the first electrode portion 613a to the base end side.

The second electrode 617 contains platinum as a main component, and includes a second electrode portion 617a formed at a predetermined position at the leading end side, which is rectangular in plan view, and a second lead portion 617b extending from the second electrode portion 617a to the base end side. The second lead portion 617b is electrically connected to the first through hole conductor 615a secured at the solid electrolyte layer 615 at the base end thereof.

Also, one electrode pad 635 is disposed at a predetermined position at the base end side of the surface of the solid electrolyte layer 615. The electrode pad 635 is connected to the first through hole conductor 615a, and further is electrically connected to the second lead portion 417b of the second electrode 417.

Next, a description is given of the porous layer 612. The porous layer 612 is disposed at a position corresponding to the first electrode portion 613a, and permits exhaust gas to pass through the porous layer 612 so as to expose gas to be measured to the first electrode portion 613a. In addition, the porous layer 612 is made of a material the main component of which is alumina.

Also, the shielding layer 610 is stacked on the solid electrolyte layer 615 via the porous layer 612, and is made of a material the main component of which is alumina. The thickness t7 (Refer to FIG. 9) of the protection main body layer 611 is 0.5 mm.

Next, a description is given of the introduction hole forming layer 625. The introduction hole forming layer 625 is provided on the second surface 650b of the solid electrolyte layer 615. The introduction hole forming layer 625 is formed of a material the main component of which is alumina, and is a dense layer having an electrical insulating property. An atmospheric air introduction hole 625a is formed at a position corresponding to the second electrode 617a toward the base end side. Therefore, atmospheric gas is permitted to pass therethrough to contact the second electrode portion 617a.

Next, a description is given of the heater portion 670. The heater portion 670 includes a dense first heater insulating layer 627 (the fourth base layer) of electrical insulating property, a dense second heater insulating layer 631 (the fourth base layer) of electrical insulating property, and a heater element 629 that generates heat by energization so as to be arranged therebetween. The heater insulating layer 627 is formed of a material the main component of which is alumina, and is stacked on the second surface 650b of the sensing portion 650. Also, the second heater insulating layer 631 is formed of a material the main component of which is alumina. Since each of the first heater insulating layer 627 and the second heater insulating layer 631 has a thickness of 0.25 mm, the thickness t8 (Refer to FIG. 9) which is a total of the thicknesses of the layers 627 and 631 is 0.5 mm. Therefore, the total thickness t8 of the first and the second heater insulating layers 627 and 631 is equal to the thickness t7 of the shielding layer 611 (that is, t7=t8).

Also, the second through hole conductor 631a and the third through hole conductor 631b are formed at predetermined positions at the base end side of the second heater insulating layer 631 so as to pass therethrough. Further, two electrode pads 635 are juxtaposed in the width direction and are disposed at predetermined positions at the base end side of the second heater insulating layer 631. One electrode pad 635 is electrically connected to the second through hole conductor 631a, and the other electrode pad 635 is electrically connected to the third through hole conductor 631b.

The heater element 629 includes a zigzag or rather comb-shaped (meandering) heater element 629a disposed at a predetermined position at the leading end side, a first heater lead portion 629b extending from one end of the heater element 629a to the base end side, and a second heater lead portion 629c extending from the heater element 629a to the base end side. The first heater lead portion 629b is electrically connected to the second through hole conductor 631a secured at the second heater insulating layer 631 at the base end side thereof. Also, the second heater lead portion 629c is electrically connected to the third through hole conductor 631b secured at the second heater insulating layer 631 at the base end thereof.

Thus, the detection element 600 according to Embodiment 3 employs zirconia as a main component and includes a sensing portion 650 having a solid electrolyte layer 615 that functions to detect a specified gas component. Also, the porous layer 612 capable of exposing the gas to be measured to the sensing portion 650 and a dense shielding layer 610 the main component of which is different from the solid electrolyte layer 615 (in this embodiment, alumina is used as the main component) are stacked on the first surface 650a of the sensing portion 650. Also, the introduction hole forming layer 625 having an atmospheric air introduction hole 625a capable of exposing the atmospheric gas to the sensing portion 650, the first heater insulating layer 627 and the second heater insulating layer 631 made of dense materials the main components of which differ from the solid electrolyte layer 650 are stacked on the second surface 650b of the sensing portion 650.

Also, the total thickness t8 of the first and the second heater insulating layers 627 and 631 is 80% or more but 120% or less of the thickness t7 of the shielding layer 611. In this embodiment, the total thickness t8 of the first and the second heater insulating layers 627 and 631 is equal to the thickness t7 of the shielding layer 611 (that is, t7=t8). Therefore, a symmetrical structure is provided, in which three members of the sensing portion 650, the shielding layer 611, and the first, the second heater insulating layers 627, 631 symmetrically overlap in the thickness direction.

Next, a description is given of a method for producing the detection element 600. Also, sintered members and unsintered members corresponding thereto are assigned the same reference numerals for convenience (Refer to FIG. 5).

First, a slurry is prepared, in which a first raw material powder containing alumina powder in an amount of 97 wt % and silica in an amount of 3 wt %, which operates as a sintering adjustment agent, and a plasticizing agent containing butyral resin and DBP are dispersed by wet blending. An unsintered shielding layer 610 corresponding to the shielding layer 610, an unsintered introduction hole forming layer 625 corresponding to the introduction hole forming layer 625, an unsintered first heater insulating layer 627 corresponding to the first heater insulating layer 627, and an unsintered second heater insulating layer 631 corresponding to the second heater insulating layer 631 are, respectively, formed using the slurry.

Also, a second slurry is prepared, in which a second raw material powder containing alumina powder in an amount of 63 wt % and silica in an amount of 3 wt % and carbon powder in an amount of 34 wt %, which operate as a sintering adjustment agent, and a plasticizing agent containing butyral resin and DBP are dispersed by wet blending. By using the slurry, an unsintered porous layer 612 corresponding to the porous layer 612 is prepared.

Also, a third slurry is prepared, in which a third raw material powder containing zirconia powder in an amount of 97 wt % and silica ($SiO_2$ powder and alumina powder in an amount of 3 wt % in total) and a plasticizing agent containing butyral resin and DBP are dispersed by wet blending. By using the slurry, an unsintered solid electrolyte layer 615 corresponding to the solid electrolyte layer 615 is formed.

In the order shown from below in FIG. 8, an unsintered second heater insulating layer 631, an unsintered heater element 629 corresponding to the heater element 629, an unsintered first heater insulating layer 627, an unsintered introduction hole forming layer 625, an unsintered second electrode 617 corresponding to the second electrode 617, an unsintered solid electrolyte layer 615, an unsintered first electrode 613 corresponding to the first electrode 613, an unsintered porous layer 612, and an unsintered shielding layer 610, etc., are stacked, wherein an unsintered stacked body is prepared.

Specifically, the unsintered heater element 629 is formed on the unsintered second heater insulating layer 631 by screen printing using a paste, the main component of which is platinum. The unsintered first heater insulating layer 627 and the unsintered introduction hole forming layer 625 are stacked on the unsintered second heater insulating layer 631 and the unsintered heater element 629.

Also, the unsintered second electrode 617 is formed on the unsintered solid electrolyte layer 615 by screen printing using a platinum paste, containing platinum in an amount of 90 wt % and zirconia powder in an amount of 10 wt %. These are stacked on the unsintered introduction hole forming layer 625 so as to arrange the unsintered second electrode 617 therebetween. After that, the unsintered first electrode 613 is formed on the unsintered solid electrolyte layer 615 by screen printing using platinum paste containing platinum in an amount of 90 wt % and zirconia powder in an amount of 10 wt %.

Next, the unsintered porous layer 612 and the unsintered shielding layer 610 are stacked on the unsintered solid electrolyte layer 615 and the unsintered first electrode 613. Thus, the unsintered stacked body is formed.

Next, after the unsintered stacked body is pressed and pressure-fitted at 1 MPa, it is cut to a predetermined size. After that, resin is removed from the unsintered stacked body, and the assembly is further subjected to regular sintering at 1500° C. for one hour, thereby obtaining a detection element 600.

After that, an unsintered detection portion protection layer corresponding to the detection portion protection layer (not illustrated) is formed on the periphery at the leading end portion of the detection element 600 using a slurry of spinel powder, titanium and alumina sol. Thereafter, the detection element 600 will be subjected to heat treatment at a sintering temperature of 1000° C. for three hours, thereby obtaining a detection element 600 having the detection portion protection layer.

As described above, in Embodiment 3, the shielding layer 610, the first and the second heater insulating layers 627 and 631 are formed of the same main component, and are made to have almost the same thickness. A symmetrical structure is provided at least at a part of the detection element in the stacking direction, along which the shielding layer 610, the first and the second heater insulating layers 627 and 631 overlap, centering around the sensing portion 650. Therefore, since stress resulting from a difference in sintering shrinkage is almost evenly (symmetrically) produced in the stacking direction centering around the solid electrolyte layer 615, warping hardly occurs, and it is possible to prevent the entirety of the element from warping. In particular, it is possible to prevent the detection element 600 from cracking due to stress resulting from a difference in sintering shrinkage when sintering, which is apt to occur in a structure having the porous layer 612 and the atmospheric air introduction hole 625 at both surfaces of the sensing portion 650. Accordingly, when sintering or attaching other members to the detection element 600, the detection element 600 is hardly subject to cracking or breakage. Further, assembly performance can be improved when producing the gas sensor 500, and a highly reliable gas sensor 500 can be provided.

Still further, portions similar to those of Embodiment 1 described above will bring actions and effects similar to those of Embodiment 1.

In the above description, the present invention is described in accordance with the embodiments. However, the present invention is not limited to Embodiments 1 to 3 described above. As a matter of course, various changes in form and detail of the invention shown and described above may be made. It is intended that such changes be included within the spirit and scope of the claims appended hereto.

Incidentally, in the above embodiments, each of the first base layer, the second base layer, the third base layer and the fourth base layer is formed of a dense material. The dense material is defined as, for example, the material having porosity of 2% or less. An example method for measuring the porosity includes: grinding a layer to be measured horizontally (along a major face of the layer); analyzing a SEM (scanning electron micrograph) image of the ground face at a magnification of 5,000 times; and calculating the porosity based on the result of analysis.

For example, in Embodiments 1 and 2, the sensing portions 250, 450, the protection portions 260, 460 and the heater portions 270, 470 are, respectively, disposed in their entirety in a direction orthogonal to the stacking direction of respective layers of the detection elements 200 and 400. However, a mode may be adopted in which only a part of these components is disposed in a direction orthogonal to the stacking direction of the respective layers of the detection elements 200 and 400. For example, only a part of the protection portions 260, 460 may be disposed in a direction orthogonal to the stacking direction of the respective layers of the detection elements 200 and 400 while the sensing portions 250, 450 and the heater portions 270, 470 are disposed in their entirety in a direction orthogonal to the stacking direction of respective layers thereof. Also, in these cases, by providing a symmetrical structure at least at a part of the stacked structure, it is possible to prevent the detection element at least at that portion from warping when sintering.

In addition, in Embodiments 1 to 3, a wide band air-fuel ratio sensor is illustrated as gas sensors 100, 300 and 500. However, the present invention is applicable to an oxygen sensor, NOx sensor, HC sensor, etc.

This application is based on Japanese patent Application No. 2007-288932 filed Nov. 6, 2007, the above application incorporated herein by reference in its entirety.

What is claimed is:

1. A gas sensor comprising:
A plate-shaped detection element configured to detect a specified gas component contained in a gas to be detected, said detection element having a symmetrical, stacked structure and comprising:
A sensing portion configured to detect a specified gas component and having a first surface and a second surface opposite the first surface, the sensing portion comprising first and second solid electrolyte layers containing a first material as a main component;
A first portion stacked on the first surface of the sensing portion and comprising one or more first base layers containing a second material as a main component different from the first material; and
A second portion stacked on the second surface of the sensing portion and comprising one or more second base layers containing the second material as a main component,
Wherein the total thickness of one or more second base layers, in a stacking direction of the sensing portion, the first portion and the second portion, is not less than 80% but not more than 120% of a total thickness of one or more first base layers, and
Wherein the first and second portions are stacked on the first and second solid electrolyte layers, respectively, so as to extend over the first and second solid electrolyte layers in a direction orthogonal to the stacking direction, so that the symmetrical stacked structure of the detection element is disposed in the recited order of the first portion, the sensing portion, and the second portion,
Wherein the sensing portion further includes an insulating layer, containing the second material, disposed between the first and second solid electrolyte layers, and
Wherein the thickness of the insulating layer is less than a thickness of each of the first and second solid electrolyte layers and each of the first and second portions, and
Both the first and second portions consist of dense layers.

2. The gas sensor according to claim 1, wherein the second portion comprises an embedded heater element configured to generate heat by energization.

3. The gas sensor according to claim 1,
wherein the sensing portion comprises: the first solid electrolyte layer having a surface defining the first surface; and the second solid electrolyte layer having a surface defining the second surface, and
wherein a thickness of the second solid electrolyte layer is not less than 80% but not more than 120% of a thickness of the first solid electrolyte layer.

4. The gas sensor according to claim 1,
wherein the first material is zirconia, and
wherein the second material is alumina.

5. The gas sensor according to claim 1, wherein:
the sensing portion includes an electrode having an electrode portion formed at a predetermined position at a leading end side of the sensing portion, and a lead portion extending from the electrode portion to a base end side of the sensing portion,
the electrode portion is wider than the lead portion in a direction perpendicular to a direction connecting the leading end side and the base end side of the sensing portion, and
the total thickness of the one or more second base layer and the total thickness of the one or more first base layers are defined at a section where the electrode is disposed.

6. The gas sensor according to claim 5, wherein:
an opening is formed through the first portion, and a porous gas introduction portion is provided in the opening, and
the electrode portion is overlapped with the porous gas introduction portion in the stacking direction.

7. The gas sensor according to claim 1, wherein the thickness of each of the first solid electrolyte layer and the second solid electrolyte layer is less than a thickness of each of the first portion and the second portion.

8. The gas sensor according to claim 1, wherein the second material of the one or more first base layers and the one or more second base layers is a dense material having a porosity of 2% or less.

9. A gas sensor comprising:
A plate-shaped detection element configured to detect a specified gas component contained in a gas to be detected, said detection element having a symmetrical stacked structure and comprising:
A sensing portion configured to detect the specified gas component and having a first surface and a second surface opposite the first surface, the sensing portion comprising first and second solid electrolyte layers containing a first material as a main component;
A first portion stacked on the first surface of the sensing portion and comprising one or more first base layers containing a second material as a main component different from the first material; and A second portion stacked on the second surface of the sensing portion and comprising one or more second base layers containing the second material as a main component, Wherein a total thickness of the one or more second base layers, in a stacking direction of the sensing portion, the first portion and the second portion, is not less than 80% but not more than 120% of a total thickness of the one or more first base layers, Wherein the first and second portions are stacked on the first and second solid electrolyte layers, respectively, so as to extend over the first and second solid electrolyte layers in a direction orthogonal to the stacking direction, so that the symmetrical stacked structure of the detection element is disposed in the recited order of the first portion, the sensing portion and the second portion, and Wherein the first base portion layer has a plate shape so as to cover an entire electrode which includes an electrode portion that is formed at a predetermined position at a leading end side of the sensing portion and a lead portion extending from the electrode portion to a base end side of the sensing portion, and Wherein the sensing portion further includes an insulating layer, containing the second material, disposed between the first and second solid electrolyte layers, and Wherein the thickness of the insulating layer is less than a thickness of each of the first and second solid electrolyte layers and each of the first and second portions, and Both of the first and second portions consist of dense layers.

10. The gas sensor according to claim 9, wherein the second portion comprises an embedded heater element configured to generate heat by energization.

11. The gas sensor according to claim 9, wherein the sensing portion comprises: the first solid electrolyte layer having a surface defining the first surface; and the second solid electrolyte layer having a surface defining the second surface, and wherein a thickness of the second solid electrolyte layer is not less than 80% but not more than 120% of a thickness of the first solid electrolyte layer.

12. The gas sensor according to claim 9, wherein the first material is zirconia, and wherein the second material is alumina.

13. The gas sensor according to claim 9, wherein the thickness of each of the first solid electrolyte layer and the second solid electrolyte layer is less than a thickness of each of the first portion and the second portion.

14. The gas sensor according to claim 9, wherein the second material of the one or more first base layers and the one or more second base layers is a dense material having a porosity of 2% or less.

* * * * *